US012723034B2

(12) United States Patent
McClure, Jr. et al.

(10) Patent No.: US 12,723,034 B2
(45) Date of Patent: Sep. 1, 2026

(54) CRYSTALLINE FORM OF EPIGALLOCATECHIN-3-GALLATE

(71) Applicant: PharmassêtX Inc., Louisville, KY (US)

(72) Inventors: George David McClure, Jr., Huntsville, AL (US); Peter York, Bradford (GB); Steven Thomas Nicholson, Bradford (GB); Linda Sharon Daintree, Bradford (GB); Aishah Ashraf, Bradford (GB)

(73) Assignee: PharmassêtX Inc., Louisville, KY (US)

( * ) Notice: Subject to any disclaimer, the term of this patent is extended or adjusted under 35 U.S.C. 154(b) by 0 days.

(21) Appl. No.: 19/381,972

(22) Filed: Nov. 6, 2025

(65) Prior Publication Data

US 2026/0167611 A1 Jun. 18, 2026

Related U.S. Application Data

(60) Provisional application No. 63/718,303, filed on Nov. 8, 2024.

(51) Int. Cl.
*C07D 311/62* (2006.01)
*A61K 31/353* (2006.01)

(52) U.S. Cl.
CPC .......... *C07D 311/62* (2013.01); *A61K 31/353* (2013.01)

(58) Field of Classification Search
CPC ............................ C07D 311/62; A61K 31/353
See application file for complete search history.

(56) References Cited

U.S. PATENT DOCUMENTS

| | | | | |
|---|---|---|---|---|
| 8,471,044 | B2 * | 6/2013 | Zaworotko | A61P 3/02 549/399 |
| 10,813,938 | B2 * | 10/2020 | Mehta | C07D 311/74 |
| 2010/0173984 | A1 | 7/2010 | Zaworotko et al. | |

FOREIGN PATENT DOCUMENTS

| | | | |
|---|---|---|---|
| CN | 109293617 | A | 2/2019 |
| WO | 95/01221 | A1 | 1/1995 |
| WO | 96/00610 | A1 | 1/1996 |
| WO | 98/36825 | A1 | 8/1998 |
| WO | 99/44733 | A1 | 9/1999 |
| WO | 99/59710 | A1 | 11/1999 |
| WO | 01/03821 | A1 | 1/2001 |
| WO | 2008/153938 | A2 | 12/2008 |
| WO | 2015/136551 | A2 | 9/2015 |
| WO | 2025/008082 | A1 | 1/2025 |

OTHER PUBLICATIONS

Anish V. Dighe, et al., Crystal Growth & Design 2022 22 (5), 3119-3127. (Year: 2022).*

Gaesser, Glenn A., et al. American Journal of Lifestyle Medicine 6.1 (2012): 4-13 (abstract). (Year: 2012).*

(Continued)

*Primary Examiner* — George W Kosturko
*Assistant Examiner* — Izabela Schmidt
(74) *Attorney, Agent, or Firm* — The Marbury Law Group, PLLC

(57) ABSTRACT

The disclosure relates to crystalline Form X of epigallocatetchin-3-gallate, compositions containing Form X, and methods of using Form X. The disclosure also relates to methods of making crystalline Form X of epigallocatetchin-3-gallate.

1 Claim, 32 Drawing Sheets

(56) References Cited

OTHER PUBLICATIONS

Brittain, Harry G. "Polymorphism in pharmaceutical solids." Drugs and the pharmaceutical sciences 95 (1999): 331-361. (Year: 1999).*
CN109293617—google translation, printed May 14, 2026. (Year: 2026).*
Adam J. Smith et al., Mol. Pharmaceutics 2013, 10, 2948-2961. (Year: 2013).*
Li, et al., "The physical and chemical stability of amorphouse (-)-epi-gallocatechin gallate: Effects of water vapor sorption and storage temperature", Food Research International 58, journal hompage: www.elsevier.com/locate/foodres, pp. 112-123, (2004).
Smith, et al., "Crystal Engineering of Green Tea Epigallocatechin-3-gallate (EGCg) Cocrystals and Pharmacokinetic Modulation in Rats", Molecular Pharmaceutics, pubs.acs.org/molecularpharmaceutics, pp. 2948-2961, (2013).
International Search Report and Written Opinion of the International Searching Authority in related International Application No. PCT/US2025/054541 dated Mar. 11, 2026.

* cited by examiner

CRYSTALLINE FORM OF EPIGALLOCATECHIN-3-GALLATE

CROSS-REFERENCE TO RELATED APPLICATION

This application claims priority to U.S. Provisional Application No. 63/718,303, filed Nov. 8, 2024, the contents of which are incorporated herein in their entirety.

TECHNICAL FIELD

The disclosure relates to a new crystalline form of epigallocatechin-3-gallate, sometimes referred to herein as crystalline Form X, compositions comprising Form X, and methods of using Form X. The disclosure also relates to processes for preparing crystalline forms of epigallocatechin-3-gallate, including Form X.

BACKGROUND

Green tea, a beverage made from the unfermented leaves of *Camellia sinensis*, contains polyphenols which are commonly known as catechins or flavonoids. Catechins are thought to be responsible for many of the biological effects of tea. Epigallocatechin-3-gallate (EGCG) is the major catechin from green tea. EGCG is a compound of interest among the green-tea-derived catechins because it exhibits a strong antioxidant effect. Furthermore, EGCG has been associated with beneficial anti-inflammatory and anti-carcinogenic effects. EGCG exerts anti-inflammatory effects on epithelial and immune cells, and enhances mucosal protective effects by regulating tight junctions.

EGCG binds to the 67-kDa laminin receptor (67LR), a laminin-binding protein overexpressed in various types of cancer, including bile duct carcinoma, colorectal carcinoma, cervical cancer, and breast carcinoma. It is presumed that EGCG activates the 67LR receptor, leading to subsequent activation of the apoptotic signaling Akt/eNOS/NO/cGMP/PKC8 pathway, whereas the upregulation of cyclic guanosine monophosphate (cGMP) (e.g., by phosphodiesterase-5 inhibitor vardenafil) acts as a rate-determining process of 67LR-dependent apoptosis. In addition, EGCG inhibits the toll-like receptor (TLR) 4 signaling through the 67LR-dependent mechanism and thereby exerts anti-inflammatory action. Activation of TLR4 leads to the activation of important pathways regulating inflammation and apoptosis such as the nuclear factor (NF)-κB, activator protein (AP)-1 through activating mitogen-activated protein kinases (MAPK), or interferon regulatory factor (IRF) 3.

EGCG also influences the cell surface growth factor receptors, mainly receptor tyrosine kinases, which participate in many processes including cell proliferation, survival, and angiogenesis. For instance, EGCG inhibited a platelet-derived growth factor receptor (PDGFR)-induced mitogenesis of vascular smooth muscle cells. Inhibition of the epidermal growth factor receptor (EGFR) by EGCG resulted in potent anti-tumor effects as demonstrated by the inhibition of cell proliferation and migration in non-small cell lung cancer cells, reduced colorectal cancer cell growth, or reduced invasion of breast cancer cells. Another cell surface receptor, the vascular endothelial growth factor receptor (VEGFR), stimulates angiogenesis and increases the growth of tumorous and atherosclerotic plaques. EGCG inhibited VEGFR and thereby partially reduced the growth of colorectal cancer cells or hepatocellular carcinoma cells. Similarly, EGCG caused the inhibition of an insulin-like growth factor (IGFR)-1 which is involved in the development of hepatocellular carcinoma, colon carcinoma, pancreatic carcinoma, and other cancers.

Elucidation of these mechanisms of action of EGCG substantiates the compound as a versatile modulator of cellular responses that may contribute to disease pathogenesis. EGCG has been shown to protect against oxidative stress-induced mitochondria-dependent apoptosis, improve endothelial function and insulin sensitivity, reduce blood pressure, protect against cardiovascular disease, decrease LDL cholesterol, increase leptin, improve glucose tolerance, protect against myocardial ischemia-reperfusion injury in a mouse model of metabolic syndrome, inhibit the effects of oxidative stress, prevent carcinogenesis, prevent and treat neurodegenerative diseases by modulating amyloid precursor protein cleavage, reduce cerebral amyloidosis in a mouse model of Alzheimer's disease, and suppress hepatic gluconeogenesis by activating the 5'-AMP-activated protein kinase (AMPK). As such, there are myriad therapeutic uses for EGCG.

Depending on the administration route in therapies utilizing EGCG, it may be desirable to improve various properties of EGCG such as chemical purity, solid state purity, powder flow, particle size and shape, stability, water solubility, and membrane permeability to obtain a desired bioavailability profile. Even a slight increase in any of these properties can offer useful biological advantages. Furthermore, it can assist the manufacturing or purification process if the stability and water solubility of the EGCG can be controlled.

EGCG may crystallize in a number of different solid forms or crystal habits, including polymorphs, cocrystals, solvates, and may exist in amorphous forms. There are currently five distinct solid polymorphs of EGCG known: Form I, Form II, Form III, Form IV, and Form V. However, as stability, water solubility, and membrane permeability for the different solid forms are not the same, the different solid forms may have greater or lesser stability and bioavailability. For example, of the known forms, Forms I and IV are considered to be the most stable. Therefore, there is a need to find new solid forms of EGCG, such as crystalline Form X, to offer different options for various therapies using EGCG.

SUMMARY

The disclosure relates in particular to crystalline Form X of epigallocatetchin-3-gallate, compositions comprising Form X of epigallocatetchin-3-gallate, and methods of using Form X of epigallocatetchin-3-gallate. The disclosure also relates to methods of preparing crystalline forms of epigallocatetchin-3-gallate.

In an embodiment, the disclosure relates to crystalline Form X of epigallocatetchin-3-gallate having an X-ray Powder Diffraction (XRPD) pattern substantially as shown in FIG. 21. Form X is surprisingly stable and has advantageous properties compared to other known crystalline forms of epigallocatetchin-3-gallate, including morphology and particle size, a faster dissolution rate, and better flow properties.

In some embodiments, the disclosure relates to compositions comprising an effective amount of Form X epigallocatetchin-3-gallate. The compositions may comprise one or more additional components, for example pharmaceutically acceptable carriers and/or excipients.

In some embodiments, the disclosure relates to methods of using crystalline Form X epigallocatetchin-3-gallate comprising administering an effective amount of Form X epigallocatetchin-3-gallate to a human patient in need thereof. The methods may be methods of treating and/or preventing a condition or disease for which EGCG is known to be effective.

In some embodiments, the disclosure relates to methods of preparing a crystal form of epigallocatetchin-3-gallate, the methods comprising mixing or contacting a fluid anti-solvent with a solution comprising EGCG in a solvent to precipitate the crystalline form of EGCG. The methods may, in various embodiments, prepare crystalline Form X epigallocatetchin-3-gallate (mSAS® Form X), crystalline Form I epigallocatetchin-3-gallate (mSAS® Form I), or crystalline Form IV epigallocatetchin-3-gallate (mSAS® Form IV). In various embodiments Form X may be administered to a human patient in solid or solution form. When delivered as a solution, Form X is not preserved when it dissolves.

Surprisingly, crystal forms of epigallocatetchin-3-gallate prepared according to the methods described herein have advantageous properties, particularly for Form X.

DESCRIPTION

The disclosure relates to a crystalline Form X of epigallocatetchin-3-gallate (Formula I):

(I)

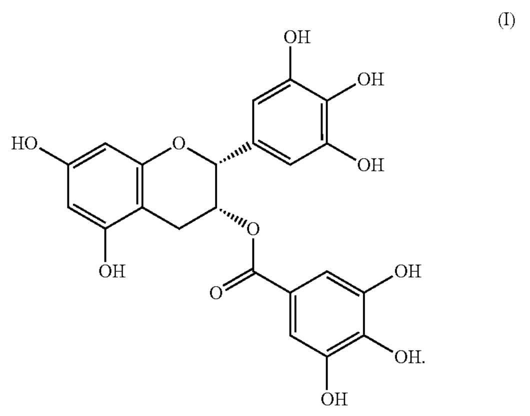 [SMILES: O=C(O[C@@H]1Cc2c(O)cc(O)cc2O[C@@H]1c1cc(O)c(O)c(O)c1)c1cc(O)c(O)c(O)c1]

The disclosure also relates to compositions comprising Form X of epigallocatetchin-3-gallate and methods of using Form X of epigallocatetchin-3-gallate, as well as to methods of preparing crystalline forms of epigallocatetchin-3-gallate, particularly crystalline Form X.

I. Form X

Form X of epigallocatetchin-3-gallate has various physical properties that distinguish it from previous forms of EGCG including, for example, chemical purity, solid-state purity, morphology, particle size, flow properties, and dissolution. Form X also exhibits relatively high polymorphic and chemical purity, and good stability.

Form X has been characterized by X-ray Powder Diffraction (XRPD), Differential Scanning calorimetry (DSC), Fourier-Transform Infra-Red Spectroscopy (FTIR), Thermogravimetric Analysis (TGA), High Performance Liquid Chromatography (HPLC), Proton Nuclear Magnetic Resonance (NMR), and Scanning Electron Microscopy (SEM).

Figure 21:
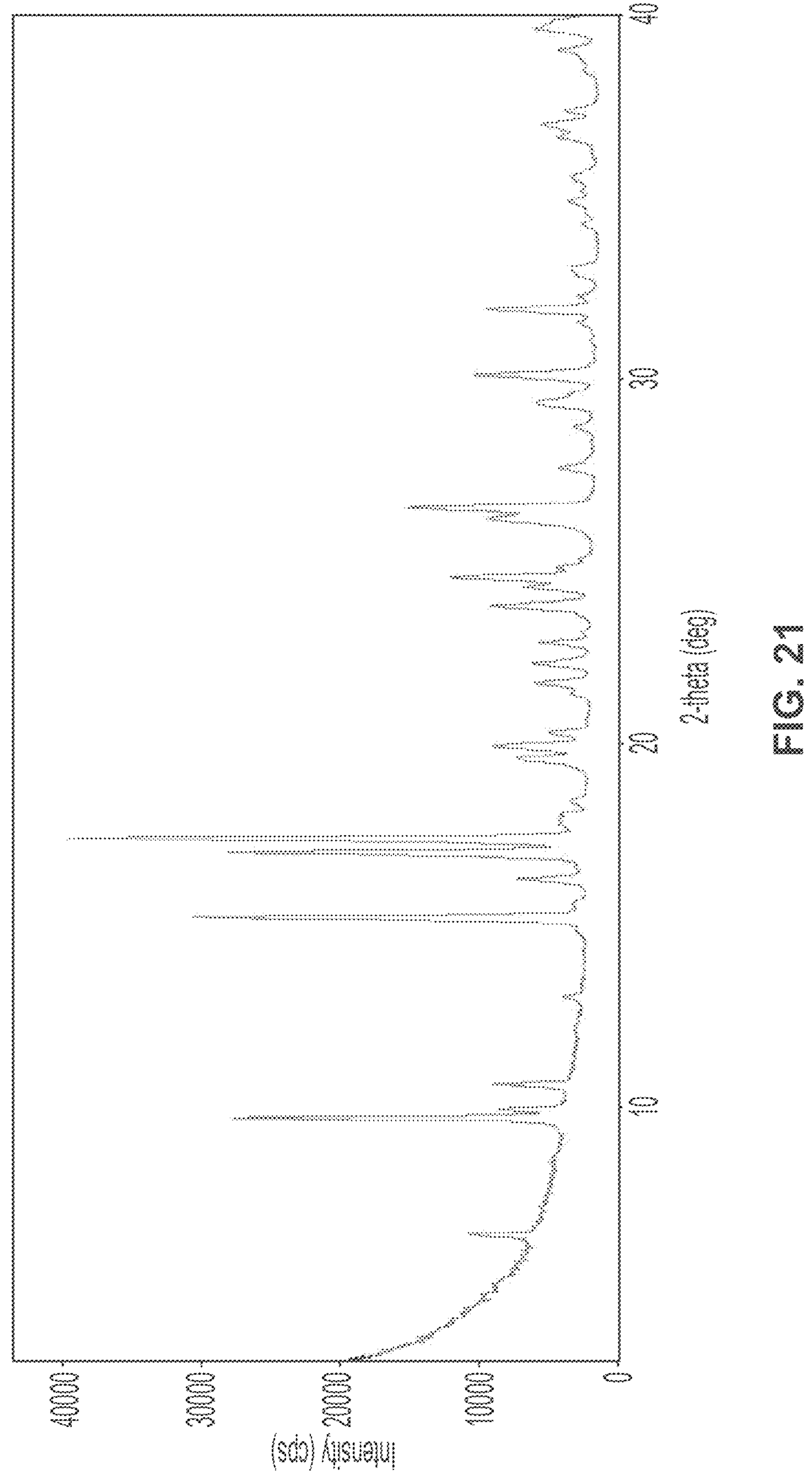
FIG. 21 shows the PXRD pattern of mSAS® Form X.

Form X has an XRPD pattern with characteristic peaks at about the following 2θ values: 6.4°, 9.7°, and 10.6° (±0.2° 2θ). Additional characteristic peaks are seen at about the following 2theta values: 13°, 15.2°, and 16.2° (±0.2° 2θ). Form X shows peaks at about the following 2theta values: 6.4°, 9.7°, 10.6° 13°, 15.2°, 16.2°, 16.9°, 17.3°, 17.8°, 18.4°, 19.6°, 19.9°, 20.3°, 21.6°, 22.2°, 22.7°, 23.0°, 23.8°, 24.3°, and 25° (±0.2° 2θ). FIG. 21 is an XRPD pattern of Form X.

Figure 22:
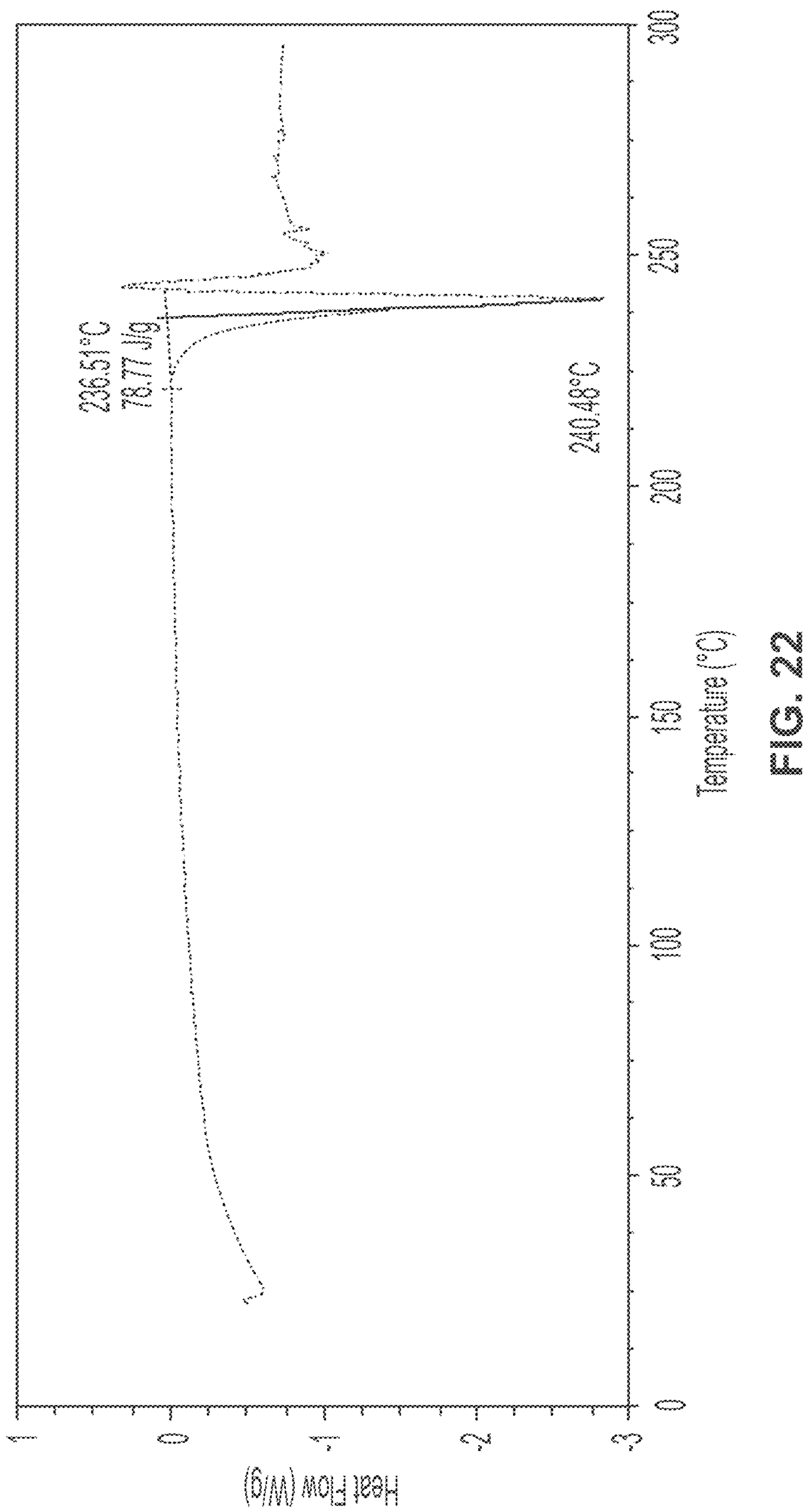
FIG. 22 shows the DSC thermal profile of mSAS® Form X.

Form X has a DSC profile exhibiting a first endothermic peak with onset ranging from 234° C. to 239° C., such as from 235° C. to 238° C., or from 236° C. to 237° C. FIG. 22 shows the DSC thermal profile of Form X.

Figure 23A:
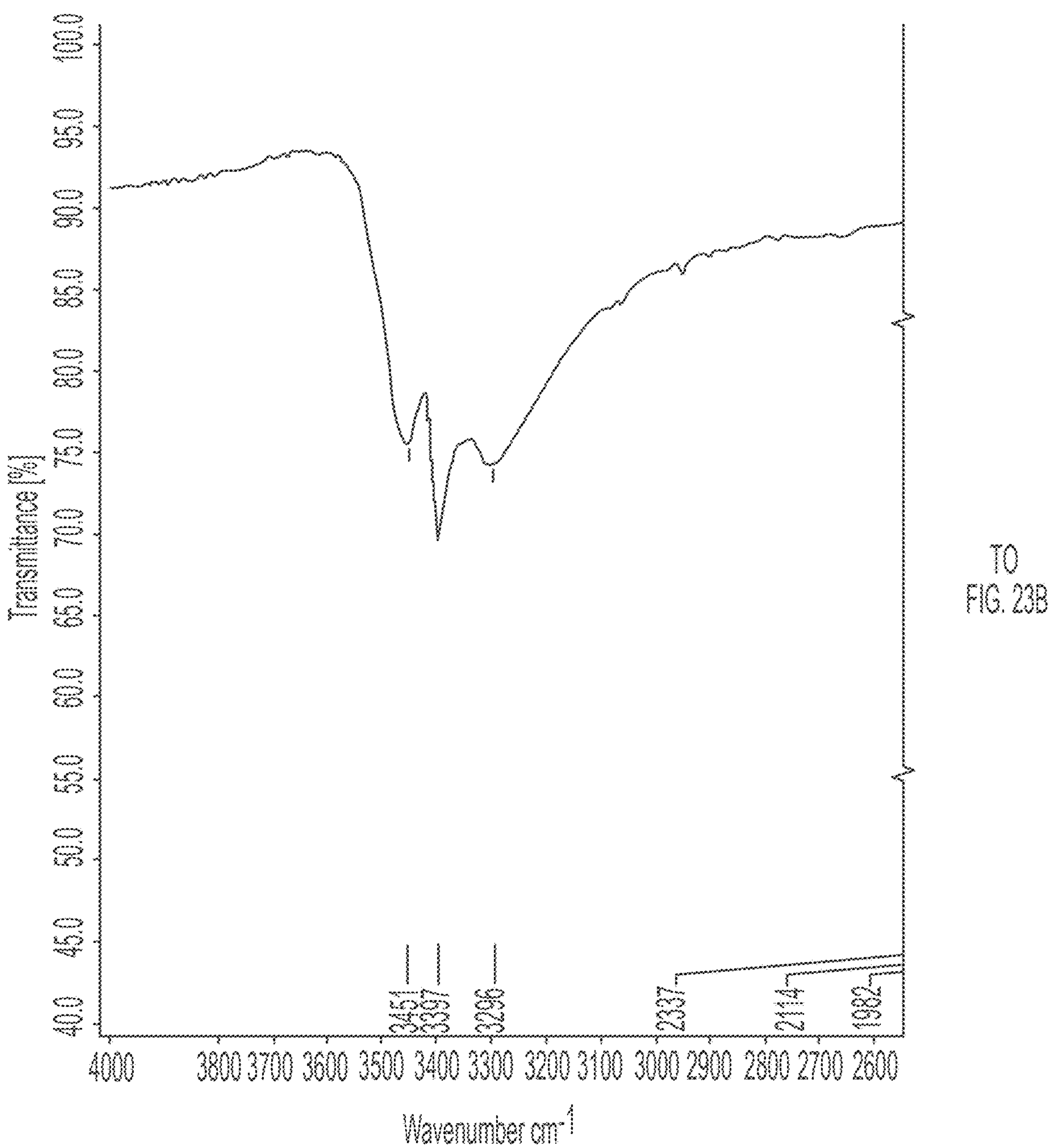
FIGS. 23A and 23B show the FTIR trace of mSAS® Form X.
Figure 23B:
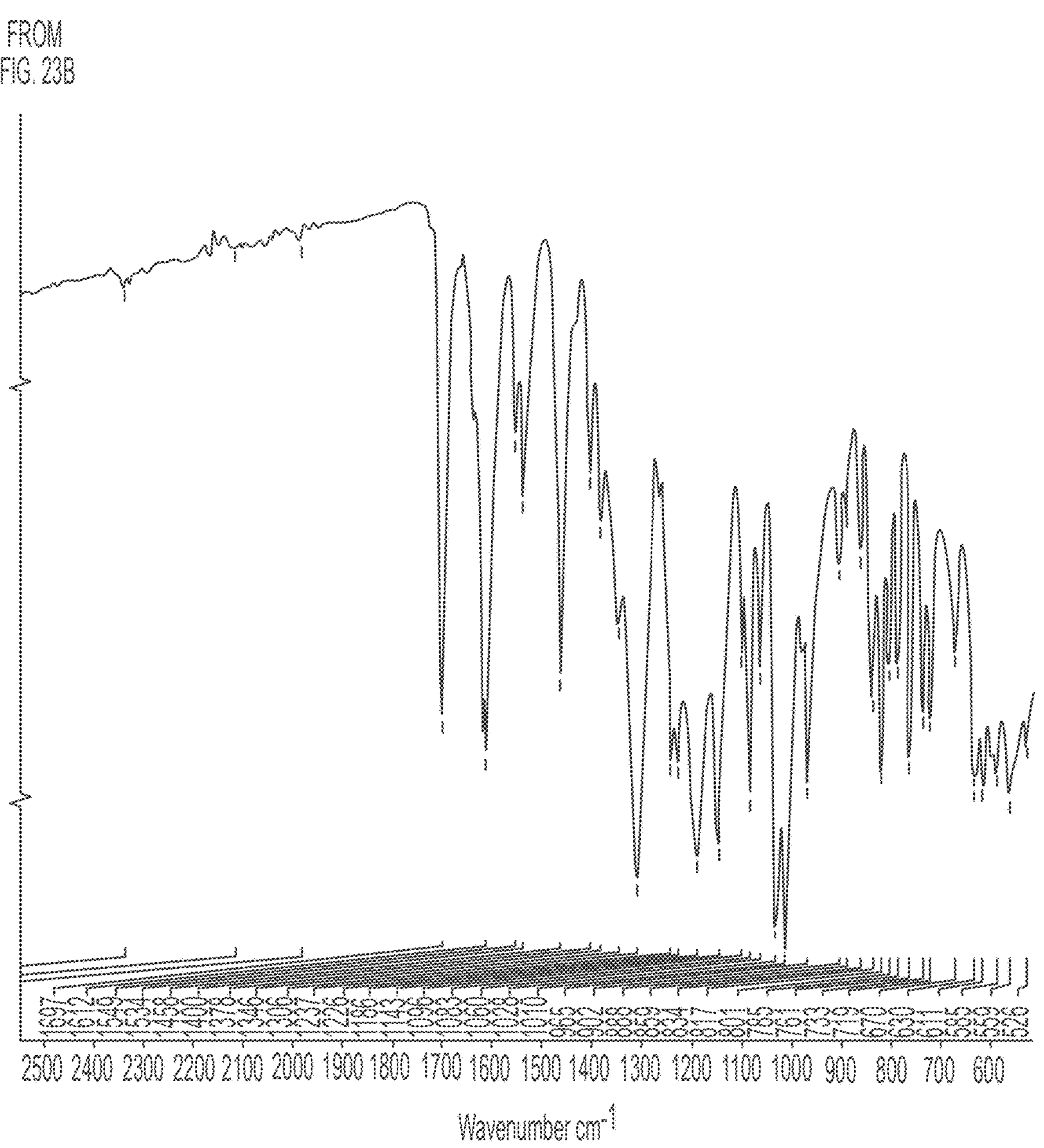
Figure 24:
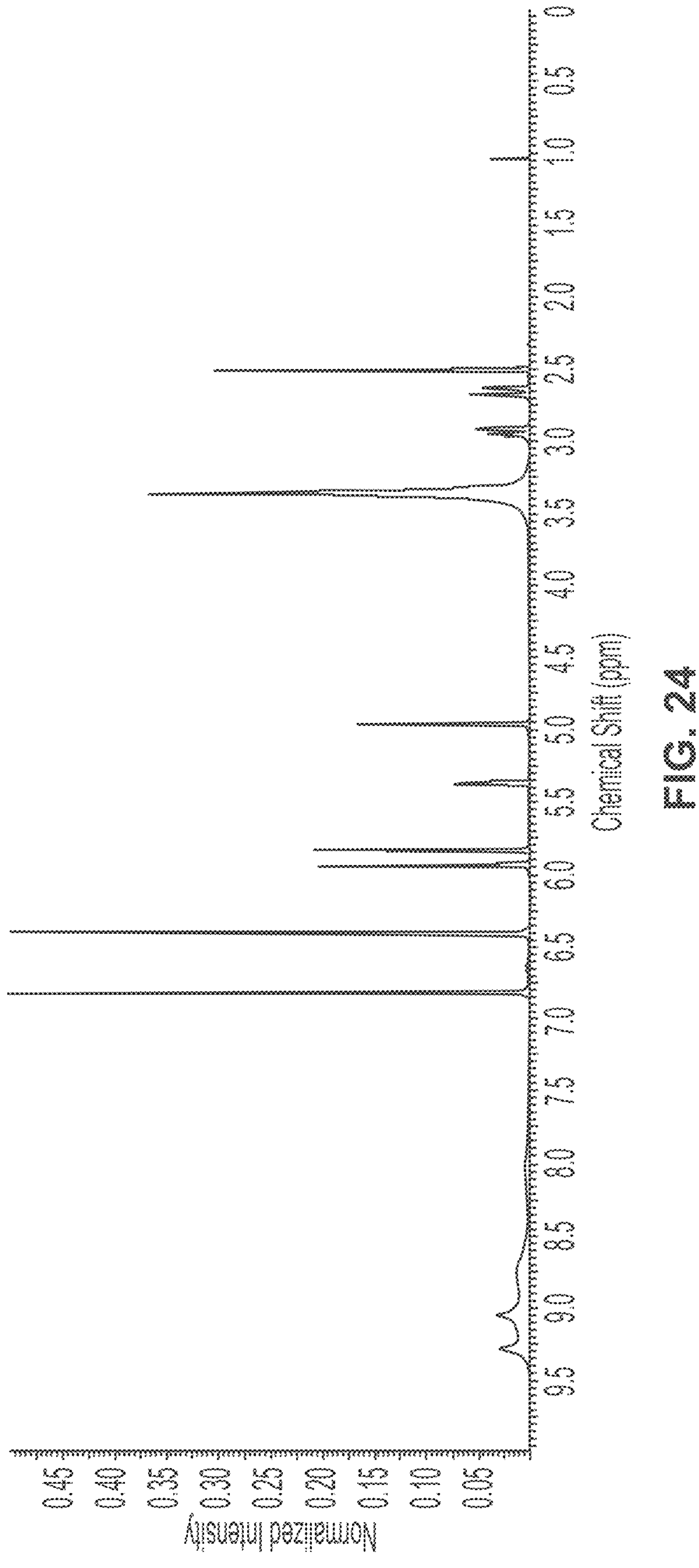
FIG. 24 shows the NMR trace of mSAS® Form X.
Figure 25:
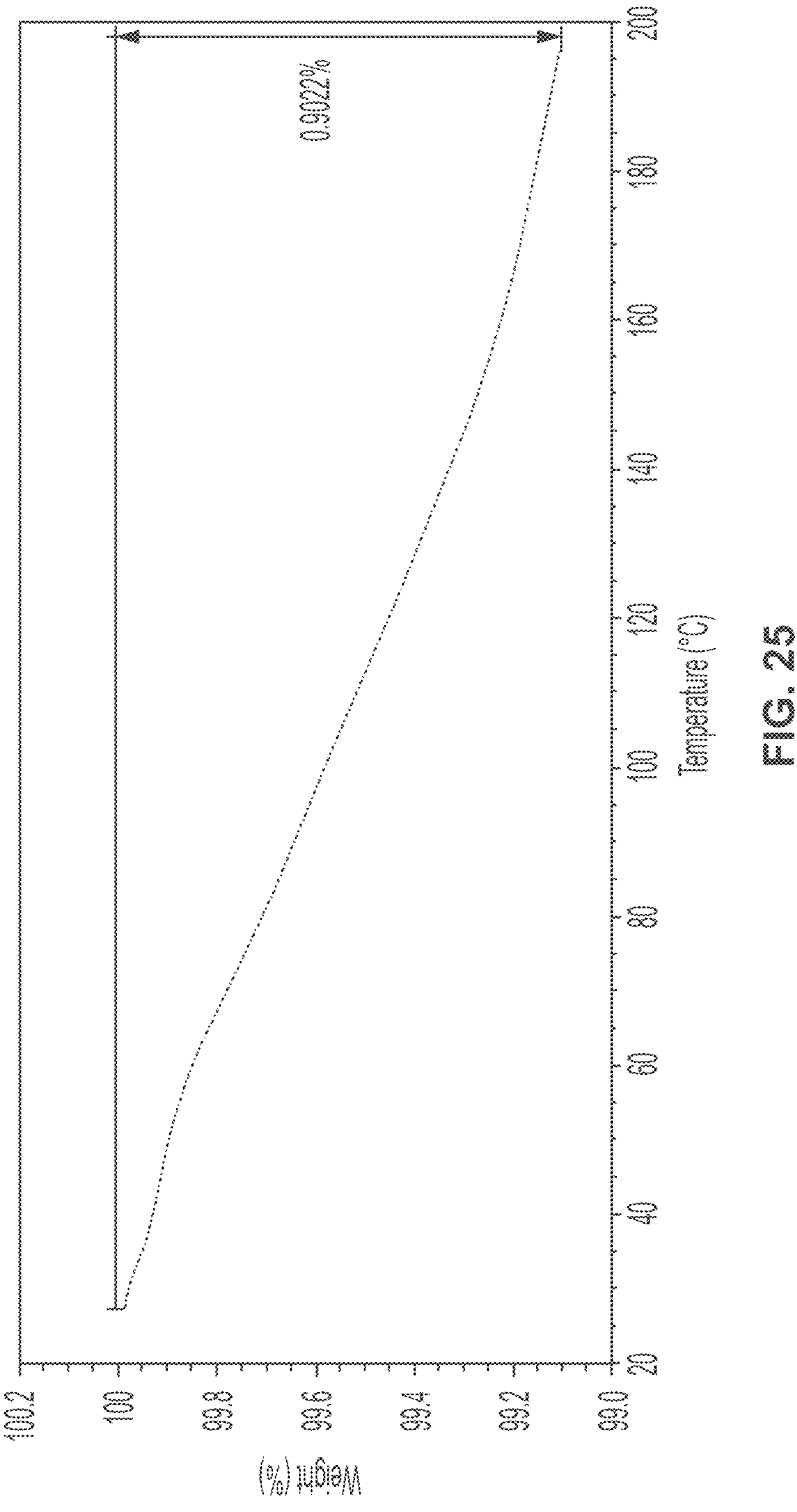
FIG. 25 shows the TGA mass profile of mSAS® Form X.
Figure 26:
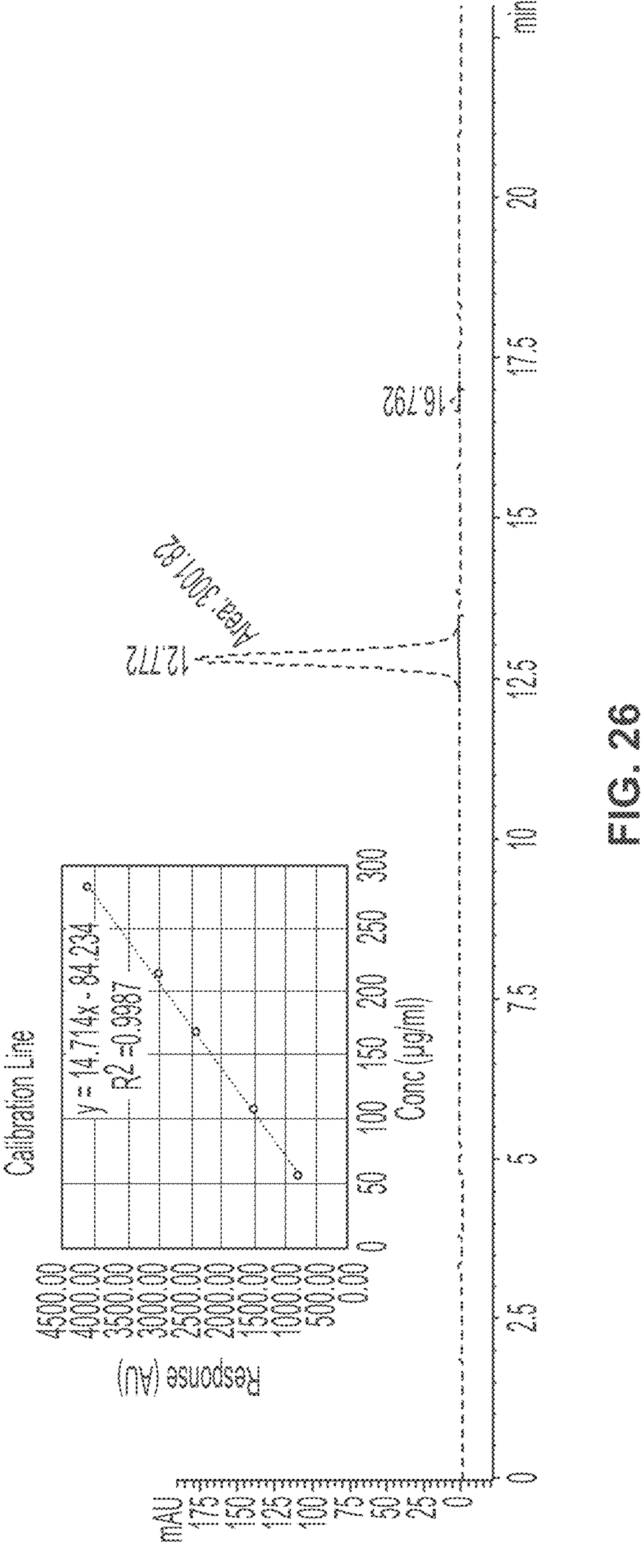
FIG. 26 shows an HPLC trace and calibration curve for mSAS® Form X.

FIGS. 23A and 23B show an IR spectrum of Form X, FIG. 24 shows an NMR trace of Form X, FIG. 25 shows a TGA profile of Form X, and FIG. 26 shows an HPLC trace and calibration curve for Form X.

Figure 27:
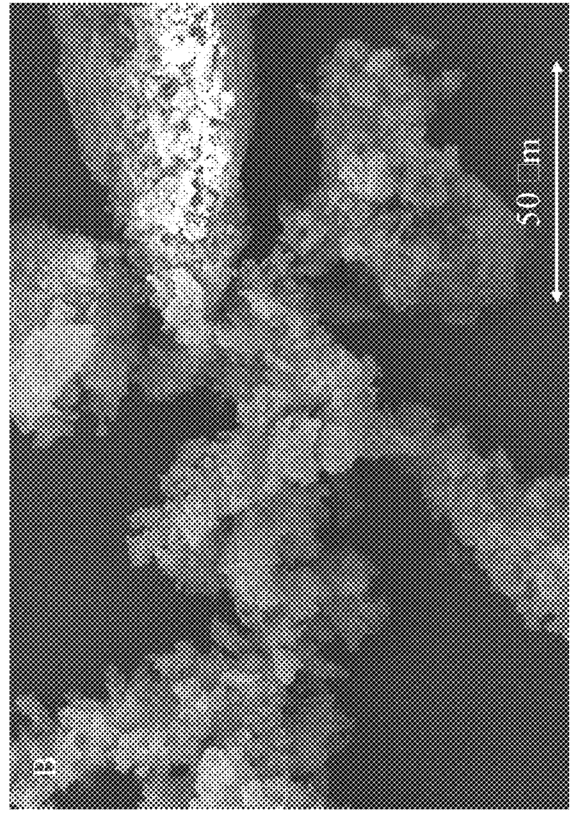
FIG. 27 shows SEM images of mSAS® Form X.
Figure 27:
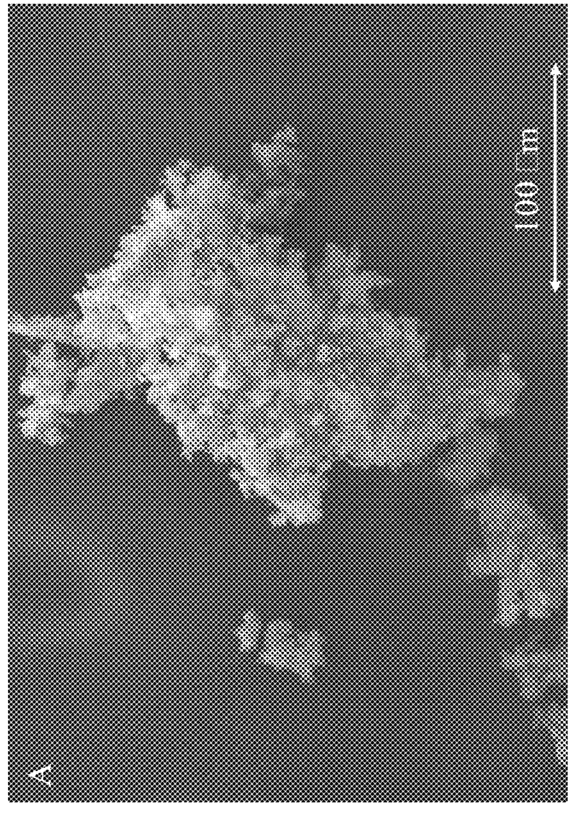

FIG. 27 shows SEM images of crystals of Form X. As can be seen, Form X displays a tabular like morphology and a more reproducibly smaller particle size. This morphology of crystalline Form X is distinct from that of Forms I-V and is ideal for administration to the intestine of a human. For example, Form I displays a more elongated and large particle morphology and size and Form IV displays either large chunky particles or needle-like feather-like particles. Advantageously therefore, no additional processing of Form X, such as milling or micronization, is required to achieve the desired particle size and morphology characteristics for purposes of administration.

Surprisingly, Form X is considered to be the most stable due to its higher melting point, relative to Forms I and IV, and enthalpy of fusion compared to the other known stable forms, Forms I and IV. Compare FIG. 27 to FIGS. 13 and 20. Form X is stable under ambient conditions, in that, for Form X, no conversion to any other polymorphic form is observed under ambient conditions, and no significant changes in chemical and/or solid-state purity are observed under ambient conditions.

Form X also has a faster dissolution rate than Forms I and IV, has beneficial flow properties, and is free flowing in contrast to Form I and Form IV with powder adhering to the glass surfaces of a glass vial after rotating the vial. See FIG. 28.

II. Compositions

The disclosure further relates to compositions comprising Form X epigallocatetchin-3-gallate. The amount of Form X present in the composition may vary, and in some embodiments may be an effective amount for treating and/or preventing a condition or disease.

Compositions according to the disclosure may be formulated comprising from about 2 mg to about 2000 mg of Form X. For example, a solid formulation such as a capsule or tablet may comprise from about 2 mg to about 750 mg of Form X of epigallocatetchin-3-gallate, such as from about 5 mg to about 500 mg, or from about 5 mg to about 300 mg. As further examples, a solid formulation such as a capsule or tablet may comprise about 2 mg, about 5 mg, about 10 mg, about 15 mg, about 20 mg, about 25 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg, including all ranges and subranges using any of the foregoing as upper and lower limits.

As another example, a liquid formulation may comprise from about 10 mg to about 2000 of Form X epigallocatetchin-3-gallate, such as from about 20 mg to about 1500 mg, or from about 30 mg to about 1000 mg. As further examples, a liquid formulation may comprise about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, or about 2000 mg, including all ranges and subranges using any of the foregoing as upper and lower limits.

Compositions according to the disclosure optionally comprise one or more additional components, for example pharmaceutically acceptable carriers and/or excipients, for example binders, lubricants, fillers, disintegrants, flavorants, sweeteners, preservatives, dyes, or the like. As non-limiting examples, useful excipients and/or carriers can include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, fructose, lactose, aspartame gums, lactose, chitosan, methylcellulose, povidone, carboxymethylcellulose, corn starch, potato starch, alginic acid, acacia, gelatin, and mixtures of two or more thereof.

III. Methods of Use

As discussed above, studies have shown that EGCG has useful antioxidant, anti-inflammatory, and anti-carcinogenic effects. However, inconsistency between the biological activity of EGCG observed in cell cultures and in vivo has been attributed to its low stability, which not only decreases its bioavailability but also leads to the formation of degradation products and prooxidant molecules with various side-effects. In view of the increased stability of Form X epigallocatetchin-3-gallate, it can be effective for treating and/or preventing any condition or disease that the known forms of EGCG have been shown to treat and/or prevent.

As an active anti-inflammatory compound, EGCG inhibits phosphorylation of p38, JNK and nuclear translocation of NF-κB, and therefore negatively regulates the expression of proinflammatory genes and proteins in various cell types. Furthermore, EGCG reduces accumulation of malfunctioning and abnormal proteins and other waste products during cellular aging. Thus, examples of conditions and diseases that Form X can be used for treating and/or preventing include but are not limited to those discussed herein such as inflammatory conditions or diseases including inflammatory bowel diseases such as Crohn's disease and ulcerative colitis, Multiple Sclerosis (MS), Rheumatoid Arthritis (RA), Sjogren's Syndrome (SS), Huntington's Disease, and COVID-19-related inflammation; cancers such as prostate cancer, breast cancer, colon cancer, colorectal cancer, mesothelioma, and stage 0-II chronic lymphocytic leukemia (CLL); cardiovascular conditions or diseases such as atherosclerosis, coronary heart disease, high blood pressure; and pulmonary conditions such as pulmonary inflammation caused by intratracheal LPS, systemic inflammation induced by intraperitoneal LPS, edema, and fibrosis.

Form X can also be used to slow the onset of and/or progression of age-related diseases such as tissue degeneration, neurodegeneration, ocular hypertension, and glaucoma. These age-related diseases are collectively characterized by increased production of reactive oxygen species (ROS) and/or insufficient cellular antioxidant capacity. The antioxidant activity of EGCG not only involves direct trapping of ROS, but also inhibition of ROS production via interaction with anti- and prooxidant proteins and chelation of potentially prooxidant metal ions. EGCG also has the ability to counteract the formation of ROS by inhibiting ROS-generating enzymes (e.g., xanthine oxidase, cyclooxygenase and lipoxygenase) and to affect the production of nitric oxide via an interaction with nitric oxide synthase (NOS).

Form X can also be used to regulate LDL-cholesterol, glucose, and insulin levels, protect against sepsis, and improve cognitive functions or prevent cognitive dysfunction.

Methods according to the disclosure therefore comprise administering an effective amount of Form X epigallocatechin-3-gallate to a patient in need thereof via formulation or without formulation, where the effective amount is the amount of EGCG needed to treat, prevent, slow the onset of, and/or slow the progression of a condition or disease for which EGCG is known to be effective.

IV. Methods of Making Crystalline Forms of Compounds of Formula I

The disclosure relates to methods of making crystalline forms of compounds of Formula I. Crystalline forms of the compounds prepared according to the methods can have unexpected advantageous and beneficial properties.

General Procedure

It has surprisingly been discovered that using an anti-solvent precipitation process, crystalline forms of the compound of Formula I may be prepared. Advantageously, the process allows for the preparation of single polymorphs of the compound of Formula I having desirable properties such as beneficial morphologies, high stability, higher purity, faster dissolution, improved flow properties, and lower residual solvent. The isolation of Form X from the anti-solvent precipitation process is particularly surprising and unexpected given that this polymorph exhibits improved stability.

The anti-solvent may in principle be any fluid consistent with achieving desired crystalline particle formation. An anti-solvent for precipitation is generally chosen such that the product, in this case the crystalline form of EGCG, is substantially insoluble therein. The role of the anti-solvent is to extract the solvent from the solution of EGCG and to precipitate crystalline particles of EGCG.

In some embodiments, the fluid anti-solvent is carbon dioxide. In some embodiments, the anti-solvent is a supercritical fluid (e.g., carbon dioxide) or a near-critical fluid. The fluid anti-solvent and the solution of the compound of Formula I may form a supercritical or near-critical mixture on contact. The fluid anti-solvent may have a pressure ranging from about 65 to about 215 bar absolute, such as from about 100 bar to about 200 bar. In some embodiments, the anti-solvent may have a temperature ranging from 40° C. to about 95° C., such as from about 45° C. to about 85° C. The fluid anti-solvent may have a density ranging from 0.20 $g/cm^3$ to 0.85 $g/cm^3$, such as from about 0.4 $g/cm^3$ to about 0.80 $g/cm^3$, from about 0.50 $g/cm^3$ to about 0.70 $g/cm^3$, or from about 0.55 $g/cm^3$ to about 0.65 $g/cm^3$.

In some embodiments, an excess of the anti-solvent is mixed or contacted with the solution of the compound of Formula I. For example, the ratio of the mass fraction of contacted anti-solvent to the mass fraction of contacted EGCG solution may be at least about 5:1, such as about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 200:1, or about 1000:1, including all ranges and subranges using any of the foregoing as upper and lower limits. For example, the ratio of the mass fraction of anti-solvent to the mass fraction of contacted EGCG solution may range from about 5:1 to about 200:1, such as from about 10:1 to about 100:1, from about 20:1 to about 75:1, or from about 30:1 to about 60:1.

In some embodiments, the solution containing the compound of Formula I is mixed with the fluid anti-solvent at a pressure ranging from about 85 to about 205 bar, or from about 100 to about 200 bar. In some embodiments, the solution containing the compound of Formula I is mixed with the fluid anti-solvent at a temperature ranging from about 40° C. to about 85° C., such as from about 45° C. to about 80° C. This may be achieved by maintaining the pressure and temperature in the precipitation chamber at the desired levels whilst the solution and anti-solvent are mixed.

The anti-solvent and the solution of EGCG may be mixed in any manner consistent with desired crystalline particle formation. In some embodiments to achieve precipitation, the anti-solvent and solution are mixed such that extraction of a solvent system of the solution occurs by the action of the anti-solvent. This may occur in the precipitation chamber with controlled temperature and pressure. In some embodiments, the anti-solvent and solution may be mixed such that dispersion and extraction of the solvent system occur simultaneously and provide approximately instantaneous homogeneous fluid mixture of the anti-solvent and solution.

The anti-solvent and the solution of EGCG may be introduced into the precipitation chamber via respective passages with respective outlets. The outlets may be arranged relative to one another such that a stream of anti-solvent may be introduced through a first passage and a stream of solution of EGCG may be introduced through a second passage in the precipitation chamber. In some embodiments, the stream of the solution of EGCG and the stream of anti-solvent may be provided to the precipitation chamber at substantially the same point. The stream of solution and the stream of anti-solvent may be co-fed into the precipitation chamber using a nozzle arrangement having co-axial passages which terminate adjacent to one another. In some embodiments, the stream of anti-solvent impinges on the stream of the solution to provide high shear and thus a high degree of contact between the anti-solvent and the solution.

In various embodiments, the methods comprise mixing a high velocity anti-solvent stream with a low velocity stream solution of EGCG. The relative velocities of the two fluid streams may be managed by varying the diameter and cross-sectional area of respective jets or nozzles for delivering the streams and further by controlling the flow rate of each fluid stream. For example, the velocity of a stream may be controlled by an orifice plate of fixed diameter. The diameter may maintain a set temperature and pressure of the orifice plate while maintaining a specific flow rate through the orifice. The velocity of the resulting stream can be calculated using the density of the fluid upstream of the orifice plate, the mass flow of the fluid, the cross sectional area of the orifice, and the differential pressure across the orifice.

In some embodiments, the anti-solvent stream velocity can range from about 10 $m/sec^{-1}$ to about 300 $m/sec^{-1}$, such as about 20 $m/sec^{-1}$ to about 150 $m/sec^{-1}$, or about 30 $m/sec^{-1}$ to about 75 $m/sec^{-1}$. In some embodiments, the velocity ratio between the anti-solvent stream and the solution stream can range from about 100:1 to about 1200:1, such as about 250:1 to about 1000:1, or about 350:1 to about 600:1.

In some embodiments, upon or subsequent to mixing, the solvent is extracted from the solution by the fluid anti-solvent to form a mixture of the solvent and the fluid anti-solvent, thereby precipitating said crystalline form of the compound of Formula I. The mixture of the solvent and the fluid anti-solvent may be removed from the precipitation chamber by a vent or other appropriate methods. In some embodiments, the crystalline form of the compound of Formula I may be recovered from the precipitation chamber. For example, this may involve de-pressurization of the precipitation chamber followed by removal of the crystalline form of the compound of Formula I. The concentration of the compound of Formula I in the solvent is greater than about 15 mg/mL, for example may be about 15 mg/mL to about 200 mg/mL, about 20 mg/mL to about 120 mg/mL, or about 20 mg/mL to about 100 mg/mL.

In some embodiments, the solvent is an organic solvent such as alcohols (e.g., C1-C6 alkanol, methanol, ethanol, propanol, isopropanol, or 1-propanol) or a mixture thereof with water. In embodiments where the solvent includes a mixture of alcohol with water, the ratio by volume of alcohol to water may be about 8:2 to about 99:1, about 85:15 to about 95:5, or about 87.5:12.5 to about 92.5:7.5.

In various embodiments, the crystalline form of the compound of Formula I is free or substantially free of amorphous material. The presence of amorphous material is disadvantageous because amorphous domains tend to be hygroscopic, leading to water-induced bridging and particle growth over time. The crystalline form of the compound of Formula I prepared according to the methods described may, in various embodiments, have less than about 10%, such as less than about 9%, less than about 8%, less than about 7%, less than about 6%, less than about 5%, less than about 4%, less than about 3%, less than about 2%, or less than about 1% by weight of amorphous material.

In some embodiments, the crystalline form of the compound of Formula I is prepared in a yield of about 25%, about 50%, about 70%, about 75%, about 80%, about 85%, about 90%, about 95%, about 96%, about 97%, about 98%, about 99%, or about 100%, including all ranges using any of the foregoing as upper and lower limits. Yield is based on the mass of the recovered crystalline form, as a percentage of the mass of the compound of Formula I starting material.

Exemplary Method of Making Crystalline Form X

In an exemplary embodiment, certain variations on one or more of the above parameters of the method may be advantageous for preparing crystalline Form X epigallocatetchin-3-gallate, as described below.

The anti-solvent can be carbon dioxide having a pressure ranging from about 85 to about 205 bar absolute, such as from about 140 to about 190, about 145 to about 180, or about 150 to about 175 bar absolute, and a temperature ranging from 40° C. to about 95° C., such as from about 50° C. to about 80° C., from about 55° C. to about 75° C., or from about 60° C. to about 70° C.

In some embodiments, the solution containing the EGCG is mixed with the fluid anti-solvent at a pressure ranging about 85 to about 205 bar absolute, such as from about 140 to about 190, about 145 to about 180, or about 150 to about 175 bar absolute, and a temperature ranging from 40° C. to about 95° C., such as from about 50° C. to about 80° C., from about 55° C. to about 75° C., or from about 60° C. to about 70° C.

Optionally, a ratio of the mass fraction of carbon dioxide to the mass fraction of EGCG solution may be at least about 20:1, such as about 25:1, about 30:1, about 40:1, about 50:1, about 60:1, about 70:1, about 80:1, about 90:1, about 100:1, or about 125:1, including all ranges and subranges using any of the foregoing as upper and lower limits. For example, the ratio of the mass fraction may range from about 30:1 to about 100:1, or about 50:1 to about 75:1.

In various exemplary embodiments, the concentration of EGCG in the solvent is greater than about 15 mg/mL, greater than about 20 mg/mL, or greater than about 25 mg/mL, for example may range from about 15 mg/mL to about 150 mg/mL, from about 20 mg/mL to about 120 mg/mL, or from about 25 mg/mL to about 100 mg/mL.

In exemplary embodiments, the solvent comprises an organic solvent such as alcohols (e.g., C1-C6 alkanol, methanol, ethanol, propanol, isopropanol, or 1-propanol) or a mixture thereof with water, for example isopropanol and/or isopropanol and water.

Exemplary Method of Making Crystalline Form I

In an exemplary embodiment, certain variations on one or more of the above parameters of the method may be advantageous for preparing crystalline Form I epigallocatetchin-3-gallate, as described below.

The anti-solvent can be carbon dioxide having a pressure ranging from about 65 to about 215 bar absolute, such as from about 75 to about 200, from about 90 to about 180, or about 100 to about 175 bar absolute, and a temperature ranging from 45° C. to about 95° C., such as from about 50° C. to about 90° C., or from about 55° C. to about 80° C.

In some embodiments, the solution containing the EGCG is mixed with the fluid anti-solvent at a pressure ranging from about 65 to about 215 bar absolute, such as from about 75 to about 200, from about 90 to about 180, or about 100 to about 175 bar absolute, and a temperature ranging from 45° C. to about 95° C., such as from about 50° C. to about 90° C., or from about 55° C. to about 80° C.

Optionally, a ratio of the mass fraction of carbon dioxide to the mass fraction of EGCG solution may be at least about 20:1, such as about 25:1, about 30:1, about 40:1, about 50:1, about 60:1, about 70:1, about 80:1, about 90:1, about 100:1, or about 125:1, including all ranges and subranges using any of the foregoing as upper and lower limits. For example, the ratio of the mass fraction may range from about 30:1 to about 100:1, or about 50:1 to about 75:1.

In various exemplary embodiments, the concentration of EGCG in the solvent is greater than about 15 mg/mL, greater than about 20 mg/mL, or greater than about 25 mg/mL, for example may range from about 15 mg/mL to about 150 mg/mL, from about 20 mg/mL to about 120 mg/mL, or from about 25 mg/mL to about 100 mg/mL.

In exemplary embodiments, the solvent comprises an organic solvent such as alcohols (e.g., C1-C6 alkanol, methanol, ethanol, propanol, isopropanol, or 1-propanol) or a mixture thereof with water, for example isopropanol and/or isopropanol and water.

Exemplary Method of Making Crystalline Form IV

In an exemplary embodiment, certain variations on one or more of the above parameters of the method may be advantageous for preparing crystalline Form IV epigallocatetchin-3-gallate, as described below.

The anti-solvent can be carbon dioxide having a pressure ranging from about 150 to about 215 bar absolute, such as from about 160 to about 210, from about 170 to about 205, or about 175 to about 200 bar absolute, and a temperature ranging from 65° C. to about 95° C., such as from about 70° C. to about 90° C., or from about 75° C. to about 85° C., or may be about 80° C.

In some embodiments, the solution containing the EGCG is mixed with the fluid anti-solvent at a pressure ranging from about 150 to about 215 bar absolute, such as from about 160 to about 210, from about 170 to about 205, or about 175 to about 200 bar absolute, and a temperature ranging from 65° C. to about 95° C., such as from about 70° C. to about 90° C., or from about 75° C. to about 85° C., or may be about 80° C.

Optionally, a ratio of the mass fraction of carbon dioxide to the mass fraction of EGCG solution may be at least about 20:1, such as about 25:1, about 30:1, about 40:1, about 50:1, about 60:1, about 70:1, about 80:1, about 90:1, about 100:1, or about 125:1, including all ranges and subranges using any of the foregoing as upper and lower limits. For example, the ratio of the mass fraction may range from about 30:1 to about 100:1, or about 50:1 to about 75:1.

In various exemplary embodiments, the concentration of EGCG in the solvent is greater than about 15 mg/mL, greater than about 20 mg/mL, or greater than about 25 mg/mL, for example may range from about 15 mg/mL to about 150 mg/mL, from about 20 mg/mL to about 120 mg/mL, or from about 25 mg/mL to about 100 mg/mL.

In exemplary embodiments, the solvent comprises an organic solvent such as alcohols (e.g., C1-C6 alkanol, methanol, ethanol, propanol, isopropanol, or 1-propanol) or a mixture thereof with water, for example isopropanol and/or isopropanol and water.

V. Crystalline Compounds of Formula I Prepared by the Methods

As described above, depending on parameters chosen, various crystalline forms of compounds of Formula I can be prepared according to the disclosed methods. For example, in an embodiment, crystalline Form X epigallocatetchin-3-gallate is prepared according to the methods described herein (mSAS® Form X). In another embodiment, crystalline Form I epigallocatetchin-3-gallate is prepared according to the methods described herein (mSAS® Form I). In yet another embodiment, crystalline Form IV epigallocatetchin-3-gallate is prepared according to the methods described herein (mSAS® Form IV).

In various embodiments, the crystalline form of epigallocatetchin-3-gallate prepared by the methods described herein is a single crystalline form (i.e. a single polymorph). In various embodiments, the crystalline form prepared is about 75%, about 80%, about 85%, about 90%, about 95%, about 96%, about 97%, about 98%, about 99%, or about 100% a single polymorph, including all ranges using any of the foregoing as upper and lower limits.

Crystalline Form X epigallocatetchin-3-gallate prepared according to the methods described herein (mSAS® Form X) surprisingly exhibit advantageous properties. For example, crystalline Form X prepared according to the methods described herein includes low residual solvents, has small particle size and tabular particle morphology, has excellent flow properties, and improved dissolution relative to other known crystalline forms of EGCG. Advantageously, one or more of these properties are obtained by the method of preparing the crystalline form, and no further processing (e.g. milling or mironization) is required. Further, crystalline Form X also exhibits relatively high polymorphic and chemical purity with improved stability compared to other known crystalline forms of EGCG.

Advantageously, crystalline Form X prepared according to the methods described herein may be a substantially pure polymorph. This may be defined by the absence of XRPD peaks characteristic of other polymorphs. For example, in some embodiments crystalline Form X prepared according to the methods described does not have XRPD peaks at about 5.2° or about 11.3° 2θ. In some embodiments crystalline Form X prepared according to the methods described does not have XRPD peaks at about 8.5° or about 13.8° 2θ. In some embodiments crystalline Form X prepared according to the methods described does not have XRPD peaks at about 5.2°, about 11.3°, about 8.5°, or about 13.8° 2θ.

Form X morphology and particle size is optimal for delivery via the intestine through displaying a more tabular like morphology and a more reproducibly smaller particle size. Form I displays a more elongated and large particle morphology and size and Form IV displays either large chunky particles or needle-like feather-like particles.

Form X has a higher chemical purity than Form I starting material but comparable purity to mSAS® processed Form I. Form IV produced by mSAS® has a lower chemical purity.

Residual solvent determination reveals that Form X has a residual solvent content (mostly water) of ~1%. Form I is a monohydrate and has a residual solvent content of ~4% corresponding to the monohydrate. Form IV has a residual solvent content of ~3% which consists of both water and Ethanol. Form IV appears to be more prone to solvent inclusion in the lattice.

Form X also has a faster dissolution rate than Forms I and IV. This is advantageous pharmaceutically and may be due to the larger surface area created from the particle size and morphology. Form X has beneficial flow properties and is free flowing in contrast to Form I and Form IV with powder adhering to the glass surfaces of a glass vial after rotating the vial.

Having described various embodiments of the disclosure, it will be apparent that modifications and variations are possible without departing from the scope of the disclosure. It is to be understood that all definitions herein are provided for the present disclosure only.

The terms "Form X," "crystalline Form X," "crystalline Form X epigallocatetchin-3-gallate," and "Form X epigallocatetchin-3-gallate" are used interchangeably herein.

The terms "epigallocatetchin-3-gallate," "EGCG," and "Formula I" are used interchangeably herein.

For purposes of the disclosure, "mixing," "contacting," and variations of these terms in methods of preparing crystalline forms of EGCG should be understood to mean any manner of combining, mixing, contacting, or the like, a fluid anti-solvent and a solution comprising EGCG in a solvent.

As used herein, "therapeutic" refers to chemicals or compounds, including small molecule drugs and large molecule drugs (also known as biologics), used for preventing or treating a condition, disorder, or disease.

As used herein, "preventing" means stopping, ameliorating, or keeping from occurring, to any degree.

Herein, the terms "slowing the progression of," "reducing," and variations thereof mean slowing the progression of, lessening, or minimizing to any degree.

Unless stated otherwise, properties described herein were measured under standard conditions, i.e. at atmospheric pressure and at a temperature of 20° C.

All 2θ values disclosed herein may be subject to an error margin of ±0.2°, or ±0.1°. Unless otherwise stated, all 20 values should be understood as ±0.2°. The powder x-ray diffraction patterns described herein and shown in the Figures were obtained using Cu—Kα radiation and an x-ray wavelength of 1.5406 Å. Melting points and enthalpies of fusion were determined using differential scanning calorimetry.

The term "polymorph" refers to a particular crystalline form of a chemical compound that can crystallize in different crystalline forms, these forms having different arrangements and/or conformations of the molecules in the crystal lattice. Polymorphs can differ in various properties such as crystal shape, density, hardness, color, chemical stability, melting point, hygroscopicity, suspensibility, dissolution rate, and biological availability. One skilled in the art will appreciate that a polymorph can exhibit beneficial effects (e.g., suitability for preparation of useful formulations, improved solubility, etc.), relative to another polymorph or a mixture of polymorphs of the same compound.

A "supercritical fluid" is a fluid at or above its critical pressure (Pc) and critical temperature (Tc) simultaneously. The pressure of the fluid may be between 1.01 and 7.0 of its critical pressure, and its temperature may be between 1.01 and 4.0 of its critical temperature. However, some fluids (e.g., helium and neon) have particularly low critical pressures and temperatures, and may need to be used under operating conditions well in excess of those critical values, such as up to 200 times the relevant critical value.

The term "near-critical fluid" encompasses both high pressure liquids, which are fluids at or above their critical pressure but below (although preferably close to) their critical temperature, and dense vapors, which are fluids at or above their critical temperature but below (although preferably close to) their critical pressure.

By way of example, a high-pressure liquid might have a pressure between about 1.01 and 7 times its Pc, and a temperature between about 0.5 and 0.99 times its Tc. A dense vapor might, correspondingly, have a pressure between about 0.5 and 0.99 times its Pc, and a temperature between about 1.01 and 4 times its Tc.

Herein, the use of the singular includes the plural unless specifically stated otherwise. The singular forms "a," "an," "the," and "at least one" are understood to encompass the plural as well as the singular unless the context clearly dictates otherwise. The expression "one or more" means "at least one" and thus includes individual components as well as mixtures/combinations.

The term "and/or" should be understood to include both the conjunctive and the disjunctive. For example, "fillers and/or binders" means "fillers and binders" as well as "fillers or binders," and expressly covers instances of either. Thus, where the disclosure refers to an element "chosen from A, B, C, D, E, and/or F," it indicates that that one of A, B, C, D, or F may be included, or a mixture of any two or more of A, B, C, D, and F may be included.

As used herein, the phrases "and mixtures thereof," "and a mixture thereof," "and combinations thereof," "and a combination thereof," "or mixtures thereof," "or a mixture thereof," "or combinations thereof," "or a combination thereof," and variations thereof are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

All ranges and amounts given herein are intended to include sub-ranges and amounts using any disclosed point as an end point, and all endpoints are intended to be included unless expressly stated otherwise. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not expressly stated, unless expressly stated otherwise. Similarly, a range given of "about 1% to 10%" is intended to have the term "about" modifying both the 1% and the 10% endpoints. The term "about" is used herein to indicate a difference of up to ±10% from the stated number, such as ±9%, ±8%, ±7%, ±6%, ±5%, ±4%, ±3%, ±2%, ±1%, or ±0.5%. Unless stated otherwise, "about" means ±10%. Likewise, all endpoints of ranges are understood to be individually disclosed, such that, for example, a range of 1% to 10% is understood to disclose both 1% and 10%.

Various components disclosed herein exist in enantiomeric form. Although a particular enantiomeric form may be recited herein, it is intended that either form may be used unless expressly stated otherwise.

EXAMPLES

FIGS. 1 through 13 illustrate results of analysis of EGCG starting material, crystalline Form I. FIGS. 14 through 20 illustrate results of analysis of EGCG crystalline Form IV. FIGS. 21 through 27 illustrate results of analysis of EGCG crystalline Form X. Also, Table 1 below gives sufficient information to allow one skilled in the art to make Form X. In a preferred embodiment for making Formula X, the process is thermodynamically stable.

Particle formation was conducted using a modified supercritical antisolvent solution technology, mSAS®.

For the mSAS® process the antisolvent and drug (in this case EGCG starting material Form I) solution were introduced continuously via respective passages into a pressurised precipitation vessel (also referred to as a precipitation chamber). The flow rates of each feed line, typically carbon dioxide as the antisolvent and a solution of drug in an organic solvent, were monitored. The pressure in the precipitation vessel was controlled and maintained by a back pressure regulator connected in line at the single outlet vent passage from the precipitation vessel. The temperature of the whole assembly was controlled. In this way, supercritical or near critical antisolvent fluid conditions were created within the precipitation vessel.

More particularly, for making Form X, the outlets of the two feed lines enter into the precipitation vessel at substantially the same point which is where the antisolvent and solution meet. To achieve a high degree of contact between the antisolvent and solution, mixing and dispersion, the antisolvent and solution are, for example, co-fed into the precipitation vessel using a nozzle arrangement having co-axial passages which terminate adjacent to one another. Alternatively, one or more streams of the antisolvent can be arranged to impinge on a stream of the solution to provide a high degree of contact between the antisolvent and the solution, mixing and dispersion. Other contact, mixing and dispersion arrangements are known with examples of suitable equipment, inter alia, from WO 95/01221, WO 96/00610, WO 98/36825, WO 99/44733, WO 99/59710, WO 01/03821, WO 2008/153938, and WO 2025/008082, the disclosures of which are incorporated herein by reference in their entireties.

Testing was performed to determine parameters such as pressure, temperature, solution composition, and solution concentration. A vessel size of 200 mL (volume of precipitation chamber) was used, and a multi-channel nozzle arrangement was used, arranged such that the carbon dioxide antisolvent impinged on a stream of the EGCG solution to provide high shear. 1H-NMR data shows that mSAS® processing did not change the chemical composition of EGCG.

Particle formation conditions that were varied are listed in Table 1, together with solid-state results. In more detail, Table 1 refers to the following particle formation conditions/results:

Yield: the % yield of the EGCG product, i.e. the mass of EGCG product collected as a percentage of the mass of EGCG starting material used ([mass collected/mass in]*100).

Mass (mg): the mass of EGCG starting material, indicated in milligrams (mg).

$CO_2$ g/min: the flow rate of carbon dioxide into the precipitation chamber, indicated in grams per minute (g/min).

TS g/min: the flow rate of the solution of EGCG into the precipitation chamber, indicated in grams per minute (g/min).

Mass fractions $CO_2$/Solution: the ratio of the mass fraction of the carbon dioxide flow rate into the precipitation chamber ($CO_2$ Flow/[$CO_2$ Flow+EGCG Solution Flow]) over the mass fraction of the solution of EGCG solution flow rate into the precipitation chamber (EGCG solution flow/[$CO_2$ Flow+EGCG solution flow]), dimensionless.

Form: the EGCG products isolated were designated as Forms I, IV, or X.

TABLE 1

| ID | % Yield | Mass (mg) | Vol mL | Solution conc. mg/mL | Solvent | % v/v | p bar | T° C. | Density g/cm$^3$ | $CO_2$ g/min | TS g/min | Mass fractions $CO_2$/Solution | Form |
|---|---|---|---|---|---|---|---|---|---|---|---|---|---|
| 1 | 39 | 600 | 20 | 30 | IPA:$H_2O$ | 9:1 | 150 | 60 | 0.694 | 40 | 0.653 | 0.984/0.016 | I |
| 2 | 17 | 600 | 20 | 30 | IPA:$H_2O$ | 9:1 | 110 | 60 | 0.358 | 40 | 0.653 | 0.984/0.016 | I |
| 3 | 55 | 600 | 20 | 30 | IPA:$H_2O$ | 85:15 | 150 | 60 | 0.694 | 40 | 0.665 | 0.983/0.017 | I |
| 4 | 9 | 600 | 20 | 30 | IPA:$H_2O$ | 87.5:12.5 | 150 | 60 | 0.694 | 40 | 0.658 | 0.984/0.016 | I |
| 5 | 29 | 600 | 20 | 30 | IPA:$H_2O$ | 85:15 | 150 | 50 | 0.700 | 40 | 0.665 | 0.983/0.017 | I |
| 6 | 45 | 600 | 20 | 30 | IPA:$H_2O$ | 9:1 | 100 | 60 | 0.290 | 40 | 0.653 | 0.984/0.016 | I |
| 7 | 18 | 600 | 20 | 30 | IPA:$H_2O$ | 9:1 | 175 | 80 | 0.523 | 40 | 0.9795 | 0.975/0.025 | I |
| 8 | 46 | 1800 | 20 | 90 | IPA:$H_2O$ | 87.5:12.5 | 175 | 70 | 0.598 | 40 | 1.235 | 0.969/0.031 | I |
| 9 | 35 | 600 | 20 | 30 | IPA:$H_2O$ | 92.5:7.5 | 175 | 80 | 0.523 | 40 | 1.01 | 0.975/0.025 | IV |
| 10 | 7 | 600 | 12 | 50 | EtOH:$H_2O$ | 9:1 | 200 | 80 | 0.594 | 40 | 1.036 | 0.974/0.026 | IV |
| 11 | 9 | 600 | 20 | 30 | IPA:$H_2O$ | 9:1 | 175 | 80 | 0.523 | 40 | 0.571 | 0.986/0.014 | IV |
| 12 | 10 | 600 | 15 | 40 | IPA:$H_2O$ | 9:1 | 175 | 80 | 0.523 | 40 | 0.653 | 0.984/0.016 | IV |
| 13 | 8 | 600 | 20 | 30 | IPA:$H_2O$ | 9:1 | 175 | 80 | 0.523 | 40 | 0.489 | 0.988/0.012 | IV |
| 14 | 15 | 600 | 20 | 30 | IPA:$H_2O$ | 91:9 | 175 | 80 | 0.523 | 40 | 0.650 | 0.984/0.016 | IV |
| 15 | 1 | 600 | 12 | 50 | EtOH:$H_2O$ | 9:1 | 150 | 60 | 0.694 | 40 | 0.663 | 0.983/0.017 | X |
| 16 | 4 | 600 | 12 | 50 | 1-propanol: $H_2O$ | 9:1 | 150 | 60 | 0.694 | 40 | 0.653 | 0.984/0.016 | X |
| 17 | 4 | 600 | 30 | 20 | IPA:$H_2O$ | 9:1 | 150 | 60 | 0.694 | 40 | 0.653 | 0.984/0.016 | X |
| 18 | 6 | 600 | 20 | 30 | IPA:$H_2O$ | 9:1 | 150 | 60 | 0.694 | 40 | 0.653 | 0.984/0.016 | X |
| 19 | 30 | 600 | 20 | 30 | IPA:$H_2O$ | 9:1 | 175 | 80 | 0.523 | 40 | 0.653 | 0.984/0.016 | X |
| 20 | 11 | 600 | 12 | 50 | IPA:$H_2O$ | 9:1 | 175 | 70 | 0.598 | 40 | 0.653 | 0.984/0.016 | X |
| 21 | 21 | 600 | 30 | 20 | IPA:$H_2O$ | 9:1 | 175 | 80 | 0.523 | 40 | 0.653 | 0.984/0.016 | X |
| 22 | 49 | 600 | 20 | 30 | IPA:$H_2O$ | 9:1 | 175 | 80 | 0.523 | 40 | 0.653 | 0.984/0.016 | X |
| 23 | 42 | 600 | 20 | 30 | IPA:$H_2O$ | 9:1 | 175 | 70 | 0.598 | 40 | 0.653 | 0.984/0.016 | X |
| 24 | 65 | 600 | 20 | 30 | IPA:$H_2O$ | 9:1 | 175 | 70 | 0.598 | 40 | 0.653 | 0.984/0.016 | X |
| 25 | 13 | 600 | 20 | 30 | IPA:$H_2O$ | 9:1 | 175 | 70 | 0.598 | 40 | 0.653 | 0.984/0.016 | X |
| 26 | 53 | 600 | 20 | 30 | IPA:$H_2O$ | 9:1 | 175 | 70 | 0.598 | 40 | 0.653 | 0.984/0.016 | X |
| 27 | 46 | 800 | 20 | 40 | IPA:$H_2O$ | 9:1 | 175 | 70 | 0.598 | 40 | 0.653 | 0.984/0.016 | X |
| 28 | 12 | 800 | 20 | 40 | IPA:$H_2O$ | 87.5:12.5 | 175 | 70 | 0.598 | 40 | 0.658 | 0.984/0.016 | X |
| 29 | 52 | 800 | 20 | 40 | IPA:$H_2O$ | 9:1 | 175 | 70 | 0.598 | 40 | 0.816 | 0.980/0.020 | X |
| 30 | 38 | 1200 | 20 | 60 | IPA:$H_2O$ | 87.5:12.5 | 175 | 70 | 0.598 | 40 | 0.658 | 0.984/0.016 | X |
| 31 | 62 | 1800 | 20 | 90 | IPA:$H_2O$ | 9:1 | 175 | 70 | 0.598 | 40 | 1.061 | 0.973/0.027 | X |

Vol mL: the volume of solvent/solvent mixture in which the EGCG starting material was dissolved.

Solution concentration mg/mL: the concentration of EGCG in the solvent/solvent mixture, indicated in milligrams per milliliter of solvent/solvent mixture (mg/mL).

Solvent: the solvent or mixture of solvents in which the EGCG starting material was dissolved.

% v/v: the ratio, by volume, of solvents when more than one solvent was used for dissolution of EGCG.

P bar: the pressure in the precipitation chamber, indicated in bars (bar).

T° C.: the temperature of the precipitation chamber, indicated in degrees Celsius (° C.).

Density g/cm$^3$: the density of the stream of carbon dioxide, indicated in grams per cubic centimeter (g/cm$^3$).

During the solid-state and purity screen, three pure solid-state forms designated Forms I, IV, or X were isolated. Disclosed embodiments Forms I and IV are already known monohydrate and anhydrous forms. Form X is a novel anhydrous polymorphic form. Yields were relatively low due to the small scale of the process, meaning that full recovery of the mass and accurate calculation of yield was challenging.

Using this process, it was found that the crystallization time needed to be long so to simulate this solvent was flushed over the sample for 45 minutes after crystallization. Run ID 22 and 23 were seeded experiments where 10 mg of crystalline seed was placed around the top of the vessel. Runs 24 and 27-31 involved using a reduced volume vessel of 100 mL. Run 25 had a reduced volume of 80 mL and Run 26 had a reduced volume of 120 mL compared to the original 200 mL vessel.

Characterization Methods $^{1}$H-NMR spectroscopy was carried out using a Bruker AVIII 400 MHz FT NMR spectrometer. Analysis parameters were 1D Proton NMR, 16 scans, 10 mg INHAL-101 dissolved in 0.8 mL deuterated DMSO.

X-ray powder diffraction was carried out using Rigaku MiniFlex 600 P-XRD. Cu—Kα radiation (λ=1.5406 Å) was used as x-ray source. Further details of the apparatus and method are set out below.

| | | |
|---|---|---|
| Rigaku MiniFlex 600 | X-Ray Generator | MiniFlex 600 W |
| | Detector | D/Tex Ultra 2 |
| | Control Software | MiniFlex Guidance (Version 3.1.8.0) |
| | Data Processing Software | PDXL2 (Version 2.8.3.0) |
| | Chiller | KUHLMOBIL 002-RB400-FF |
| Analysis Parameters | Scan Range | 3-40° |
| | Step Size | 0.020° |
| | Scan Speed | 0.2°/min |
| | Rotation | On |
| | Voltage | 40 kV |
| | Current | 15 mV |
| Incident Optics | Incident Parallel Slit | 2.5° |
| | Incident Slit | 1.250° |
| | Length Limiting Slit | 10 mm |
| Receiving Optics | Receiving Slit #1 | 13 mm (Open) |
| | Receiving Slit #2 | 13 mm (Open) |
| | Receiving Parallel Slit | 2.5° |
| | Filter | None |
| Sample Preparation | Evenly distribute the sample into the cavity of a low background sample holder. Using a microscopic slide compress the powder into the cavity ensuring that the sample surface is even and flush with sample holder. Wipe off any excess powder. | |
| Data Recording | Electronic | Save data as .ras, .asc, .raw, and .txt |

Differential scanning calorimetry was carried out using a DSC Q2000. Further details of the apparatus and method are set out below.

| | | |
|---|---|---|
| QSeries DSC2000 | Control Software | QSeries |
| | Data Acquisition software | QSeries |
| | Data Processing Software | TA Instruments Universal Analysis 2000 |
| | Chiller | TA Refrigerated Cooling System 90 |

| | | |
|---|---|---|
| Analysis Parameters | Equilibrium temperature | 30° C. |
| | Equilibrium time | 600 seconds |
| | Heat rate | 10° C./min |
| | Final temperature | 300° C. |
| Sample Preparation | Weigh accurately 1-5 mg sample into an aluminium vented crucible. Compress the powder into the cavity of the crucible. | |
| Data Recording | Electronic | Save data as .ras, .asc, .raw, and .txt |

Thermogravimetric analysis was carried out using a TGA Q5000. Further details of the apparatus and method are set out below.

| | | |
|---|---|---|
| TGA Q5000 | Control Software | QSeries |
| | Data Acquisition software | QSeries |
| | Data Processing Software | TA Instruments Universal Analysis 2000 |

| | | |
|---|---|---|
| Analysis Parameters | Equilibrium temperature | 30° C. |
| | Equilibrium time | 600 seconds |
| | Heat rate | 10° C./min |
| | Final temperature | 300° C. |
| Sample Preparation | Weigh accurately 5-15 mg sample into a 50 μL platinum crucible. Compress the powder into the cavity of the crucible. | |
| Data Recording | Electronic | Save data as .ras, .asc, .raw and .txt |

High performance liquid chromatography was carried out using Agilent 1100 series HPLC (binary pump, auto-sampler, column oven, DAD detector, (no degasser)). Further details of the apparatus and method are set out below.

Column: Phenomenex Luna C18 5×150×190 μm with a 100 Å pore size

Column temperature: 30° C.

UV detection: 280 nm

Flow rate: 1.0 mL/min

Injection volume: 10 μL

Standard: Starting API—assume 95.4% potency—Also take away wet % from loss on drying (place 30-100 mg of sample in a glass vial without lid in an oven at 105° C. for 3 hours—measure change in mass)

Mob Phase A: Water (0.1% phosphoric acid)—approximately 1.1 mL of 85% phosphoric acid per liter Mob Phase B: Methanol (0.1% phosphoric acid)—approximately 1.1 mL of 85% phosphoric acid per liter Diluent: Water+0.1% phosphoric acid—approximately 1.1 mL of 85% phosphoric acid per liter Stock Solution A: 0.5 mg/mL EGCG (25 mg in 50 mL diluent)

Stock Solution B: 0.5 mg/mL EGCG (25 mg in 50 mL diluent)

Stock Solution C: 0.5 mg/mL EGCG (25 mg in 50 mL diluent)

Working Reference, A: 300 μg/mL (6 mL of stock A diluted to 10 mL with diluent)

Working Reference, B: 300 μg/mL (6 mL of stock A diluted to 10 mL with diluent)

Sample Prep: 300 μg/mL (25-35 mg in 100 mL diluent)

Wash solution: diluent

Target range: 50-400 μg/mL

Time: 23 minutes

The HPLC gradient is shown below:

| Time | % A | % B |
|---|---|---|
| 0 | 80 | 20 |
| 5 | 80 | 20 |
| 7 | 76 | 24 |
| 10 | 76 | 24 |
| 18 | 27.2 | 52.8 |
| 18.01 | 80 | 20 |
| 23 | 80 | 20 |

The HPLC calibration is shown below:

| Cal Number | Volume of stock solution | Dilution volume | Concentration |
|---|---|---|---|
| 1 | 1 mL (A) | 10 mL | 50 μg/mL |
| 2 | 2 mL (B) | 10 mL | 100 μg/mL |
| 3 | 4 mL (A) | 10 mL | 200 μg/mL |
| 4 | 6 mL (B) | 10 mL | 300 μg/mL |
| 5 | 8 mL (A) | 10 mL | 400 μg/mL |

The HPLC accuracy standards are shown below:

| Acc. Standard Number | Volume of stock solution | Dilution volume | Concentration |
|---|---|---|---|
| 1 | 2 mL (C) | 10 mL | 50 μg/mL |
| 2 | 4 mL (C) | 10 mL | 200 μg/mL |
| 3 | 6 mL (C) | 10 mL | 400 μg/mL |

The HPLC testing sequence is shown below:
Blank
W Ref A×3
W Ref B×3
Blank
Acc Std 1×3
Acc Std 2×3
Acc Std 3×3
Cal 1
Cal 2
Cal 3
Cal 4
Cal 5
W Ref B
Blank
Sample(s)×2
W Ref B
Blank The HPLC checks are shown below:
Initial blank acceptable
Final blank carryover check
W Ref A and B×3 are repeatable (<2% RSD)
Retention time 11.5±2
Specificity-check for interfering peaks
Linearity—$r^2$>0.998
Range—between 50-400 μg/mL
Accuracy—triplicate injections at 3 concentrations over the range (98-102% recovery=pass)
Precision—RSD of the accuracy samples <2%

SEM was carried out using HIROX SH4000M. Further details of the apparatus and method are set out below.

| | |
|---|---|
| Scanning Electron Microscope | HIROX SH4000M |
| Sputter Coater | SEC MCM-100P |

| | |
|---|---|
| Specimen Holders | Agar G301, 0.5” specimen stubs<br>Agar G3347N, 12 mm carbon tabs<br>Coating - Gold |

| | | |
|---|---|---|
| Sample Preparation | Apply carbon tab to specimen stub and remove backing tape. Use a spatula to place sample on carbon tab, gently tap stub to remove excess material. Repeat procedure if necessary to ensure even coating of sample across carbon tab. | |
| Analysis Parameters (Sputter Coater) | Coating Material | Gold |
| | Current | 20 mA |
| | Coating time | 2 minutes |
| | Coating thickness | 30 nm |
| Analysis Parameters (SEM) | Vacuum | High vacuum mode |
| | Specimen working distance | 9.8-10.2 mm |
| | Beam spot size | 3.0 μm |
| | Voltage | 20.0 kV |
| Analysis Method | Insert sample stubs into SEM chamber, close chamber and allow vacuum to be reached before turning on electron beam. Raise sample holder to working distance. Navigate sample, focus image and take representative scans of sample at specified magnifications (shown below). | |
| Typical image magnifications | 80×<br>300×<br>1200×<br>2400×<br>5000× | |
| Data Storage | Store images in .TIFF format (uncompressed) at 2048 × 1887 resolution. | |

Form I (Starting Material)

Figure 2:
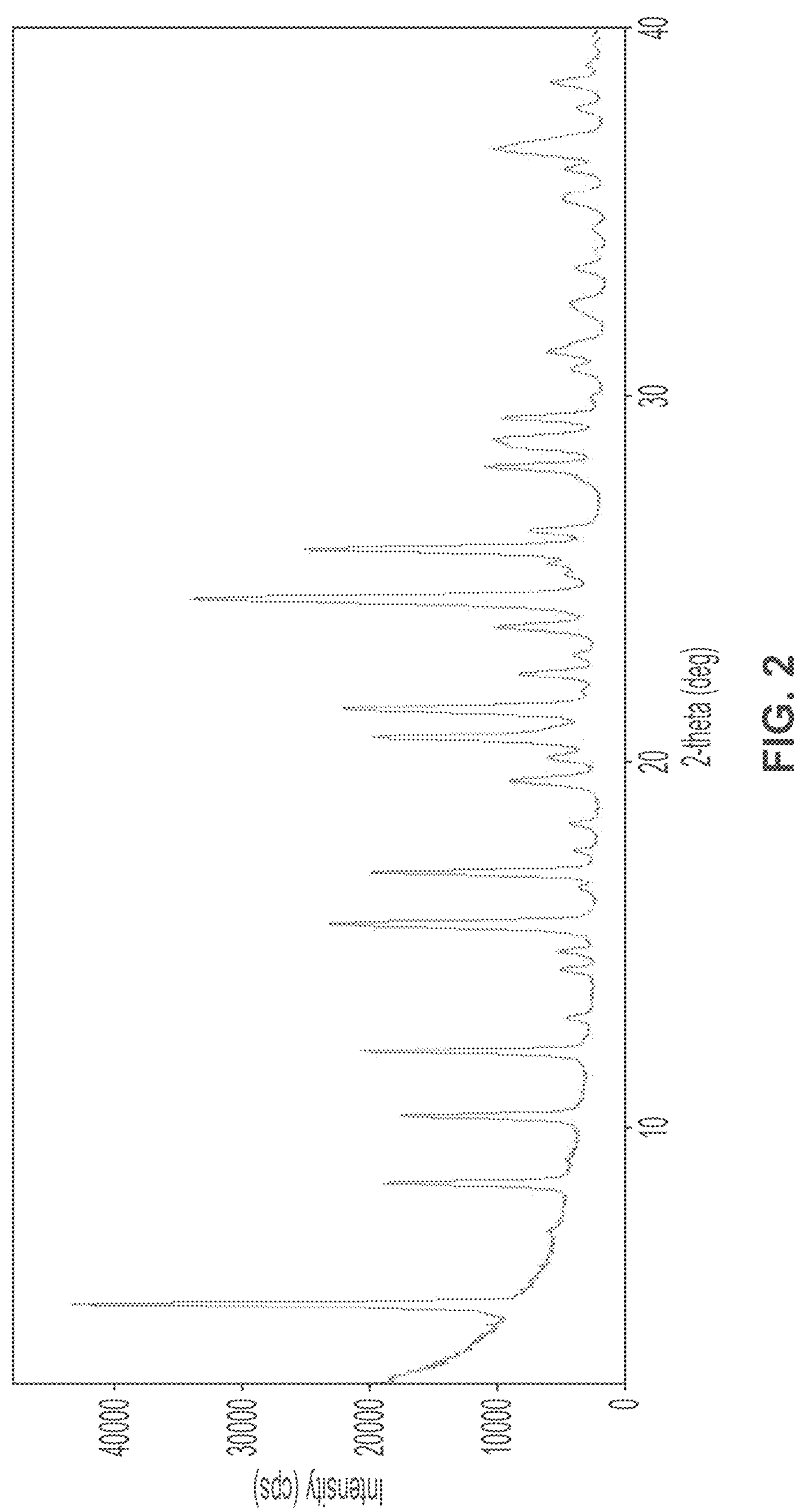
FIG. 2 shows the PXRD pattern of EGCG starting material (Form I).

The PXRD pattern of EGCG Starting Material (Form I) is shown in FIG. 2. Peak positions are set out in Table 2 below.

TABLE 2

| 2-theta (°) | Relative intensity (a.u.) |
|---|---|
| 5.18 | 4155.57 |
| 7.16 | 260.98 |
| 8.5 | 2035.25 |
| 9.16 | 257.39 |
| 10.34 | 1864.09 |
| 12.12 | 2156.23 |
| 13.04 | 197.68 |
| 14.36 | 294.46 |
| 14.86 | 338.16 |
| 15.62 | 3416.55 |
| 15.78 | 225.21 |
| 16.6 | 162.74 |
| 17.04 | 2503.06 |
| 17.62 | 302.06 |
| 18.34 | 271.45 |
| 19.54 | 1233.02 |
| 20.2 | 669.66 |

TABLE 2-continued

| 2-theta (°) | Relative intensity (a.u.) |
|---|---|
| 20.74 | 3340.69 |
| 21.52 | 3747.6 |
| 22.02 | 61.79 |
| 22.48 | 792.93 |
| 22.98 | 125.97 |
| 23.76 | 1089.42 |
| 24.52 | 6019.49 |
| 25.2 | 126.06 |
| 25.48 | 284.52 |
| 25.9 | 3723.04 |
| 26.42 | 913.47 |
| 27.88 | 415.02 |
| 28.18 | 1351.96 |
| 28.68 | 754.01 |
| 28.92 | 1922.1 |
| 29.52 | 1253.44 |

Selected characteristic X-ray diffraction peaks for EGCG Starting Material (Form I) are 5.2°, 8.5°, and 12.1° 2θ (±0.2° 2θ).

Figure 3:
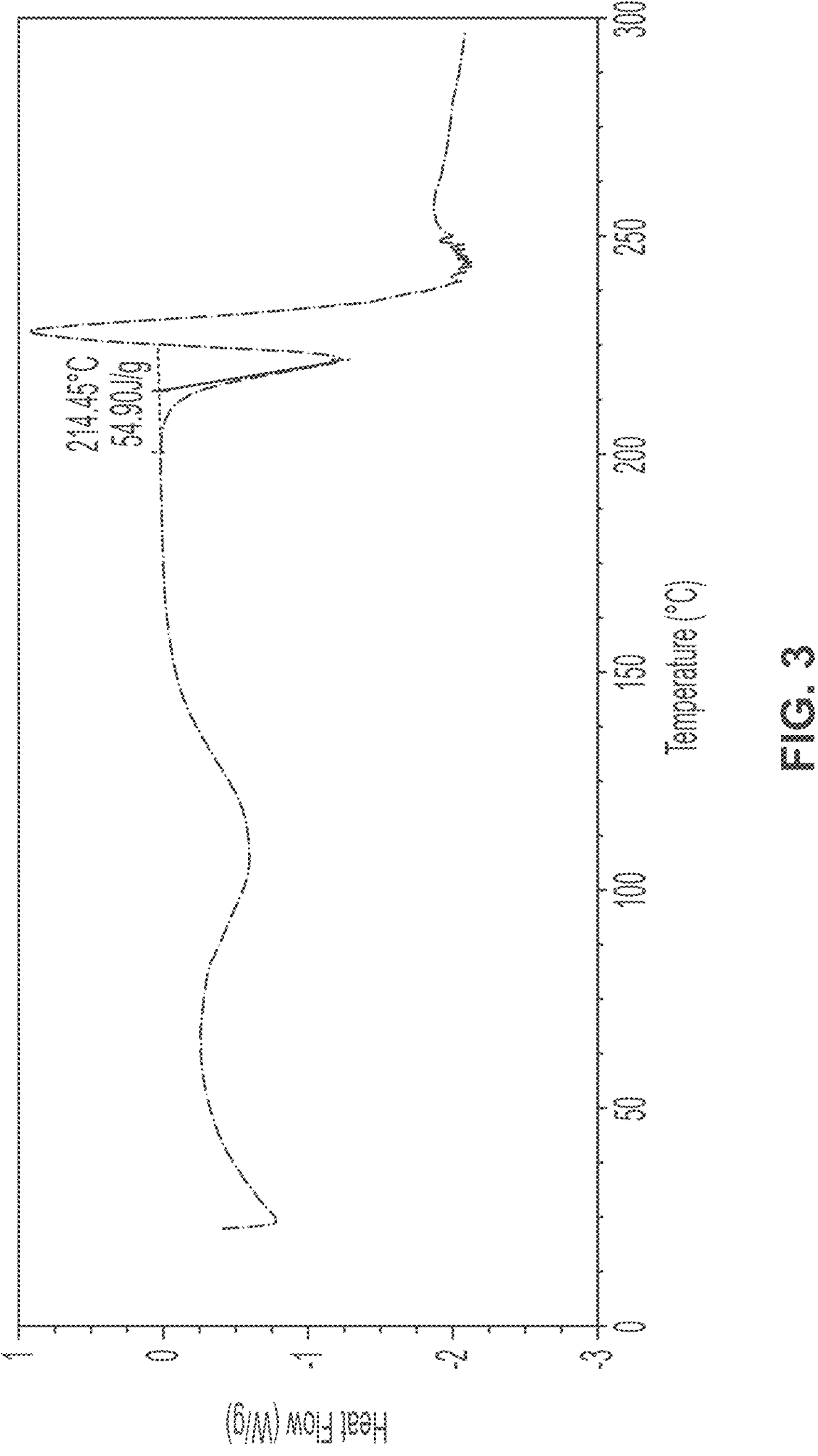
FIG. 3 shows the DSC thermal profile of EGCG starting material (Form I).

FIG. 3 shows the thermal analysis of EGCG Starting Material (Form I). EGCG Starting Material (Form I) appears to initially go through a dehydration step before melting at a higher temperature. Its melting point and enthalpy of fusion are lower than Form X indicating that it is metastable and its dehydration occurs at a low temperature.

Figure 1:
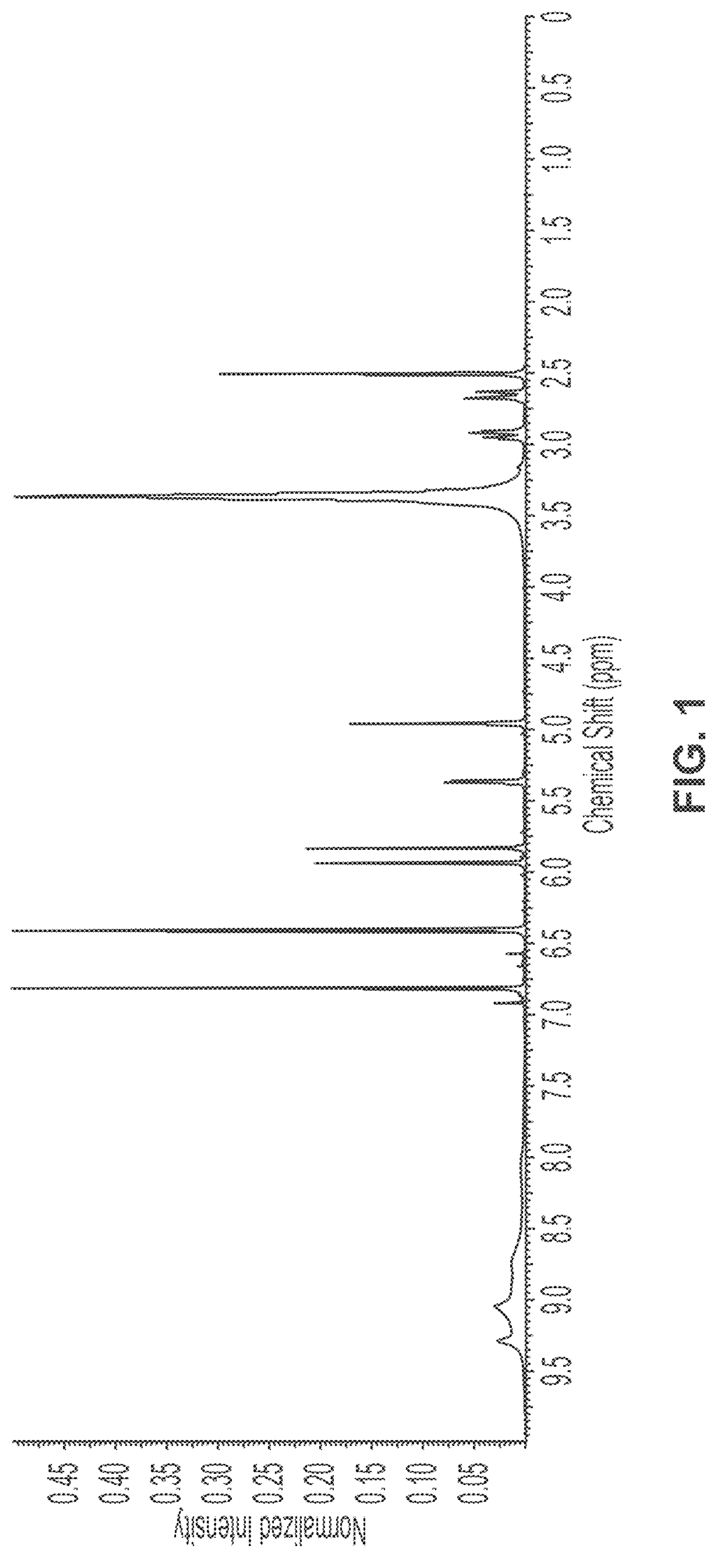
FIG. 1 shows the NMR trace of EGCG starting material (Form I).
Figure 4:
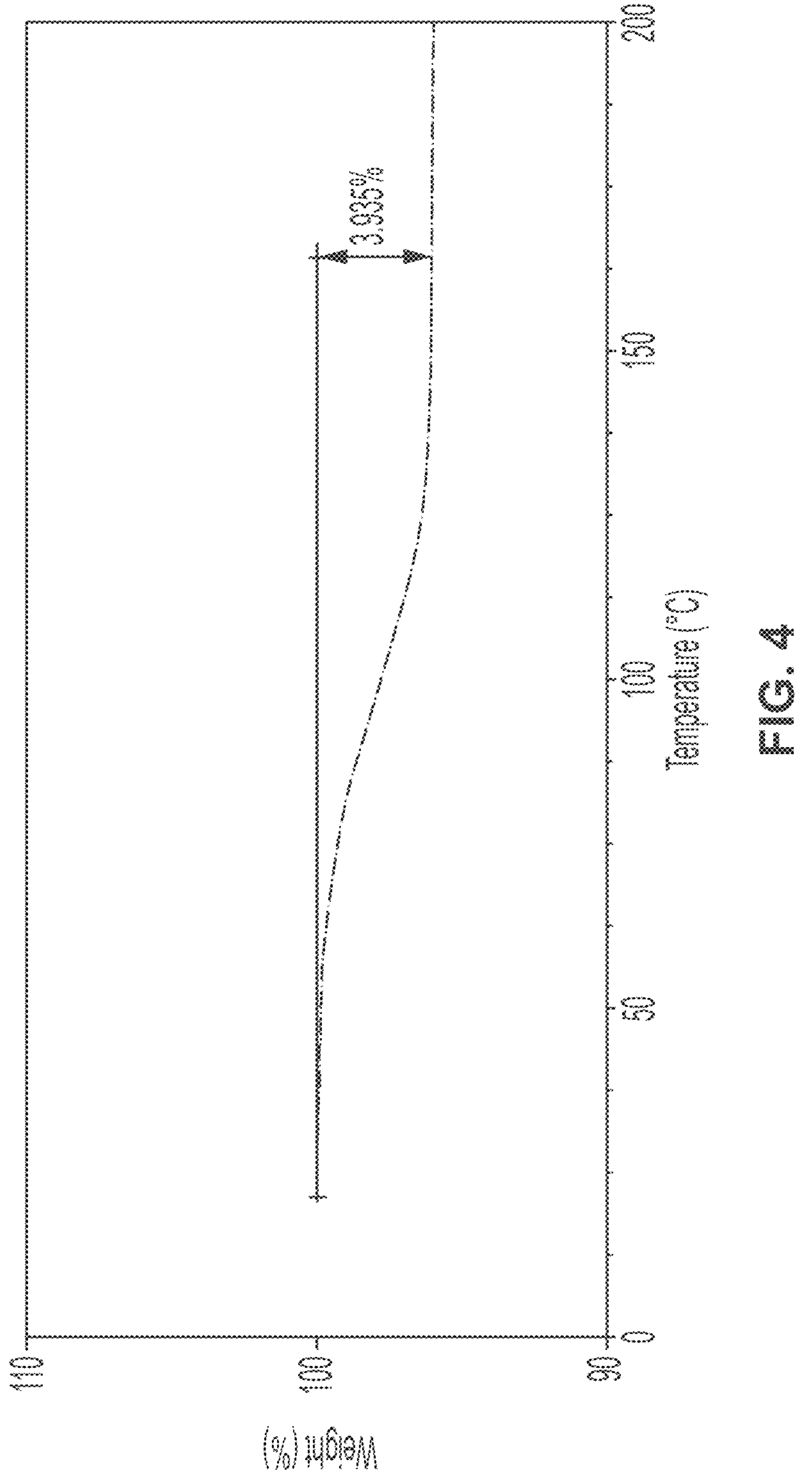
FIG. 4 shows the TGA mass profile of EGCG starting material (Form I).

FIGS. 1 and 4 show NMR and TGA profiles, respectively. As shown, there is water present and its water content is around 3.9% indicative of a monohydrate. NMR also reveals that there are a number of small impurity peaks which is reflected in its Certificate of Analysis as an EGCG purity of 95.4% based on dry matter weight.

Figure 5A:
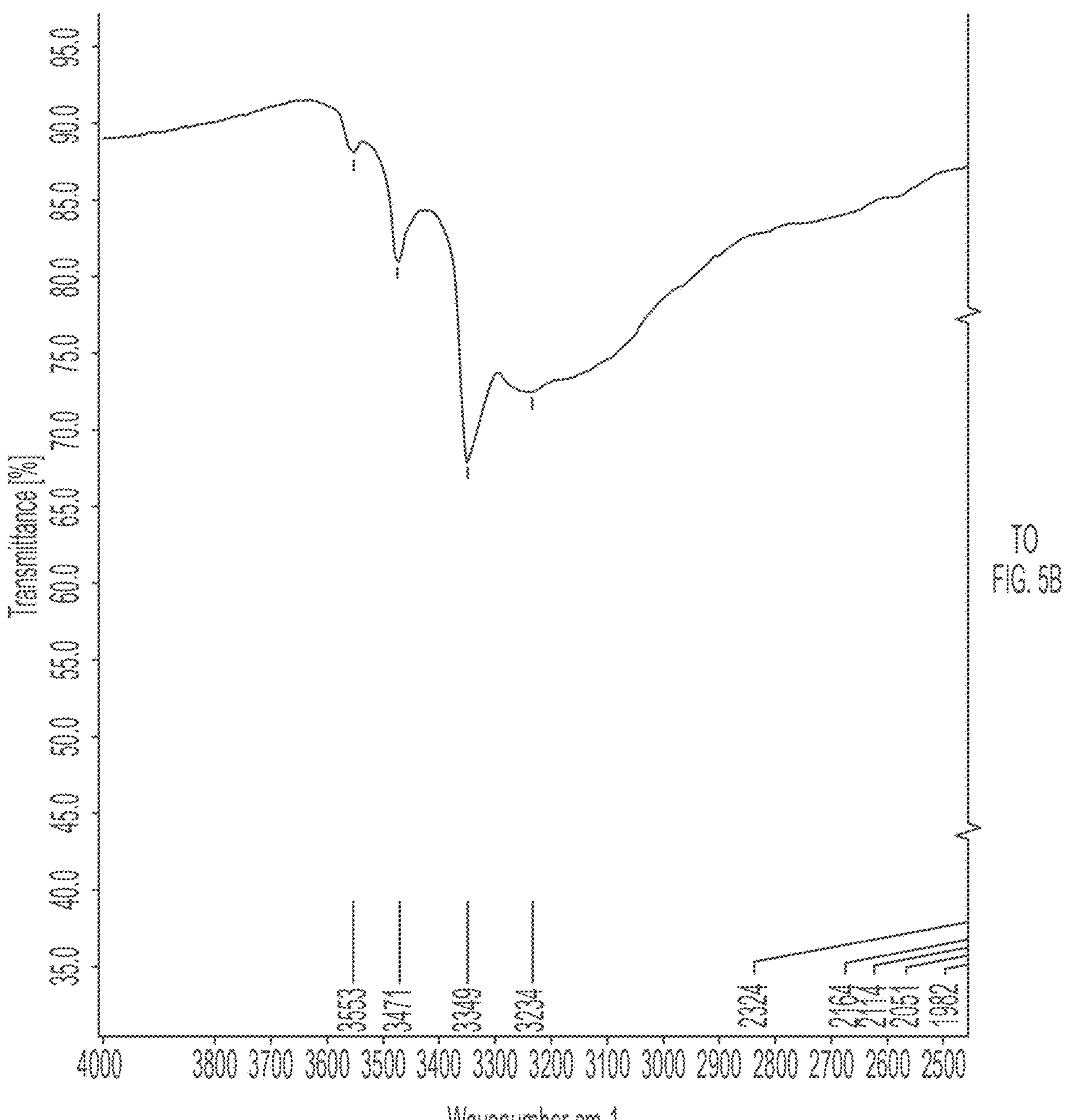
FIGS. 5A and 5B show the FTIR trace of EGCG starting material (Form I).
Figure 5B:
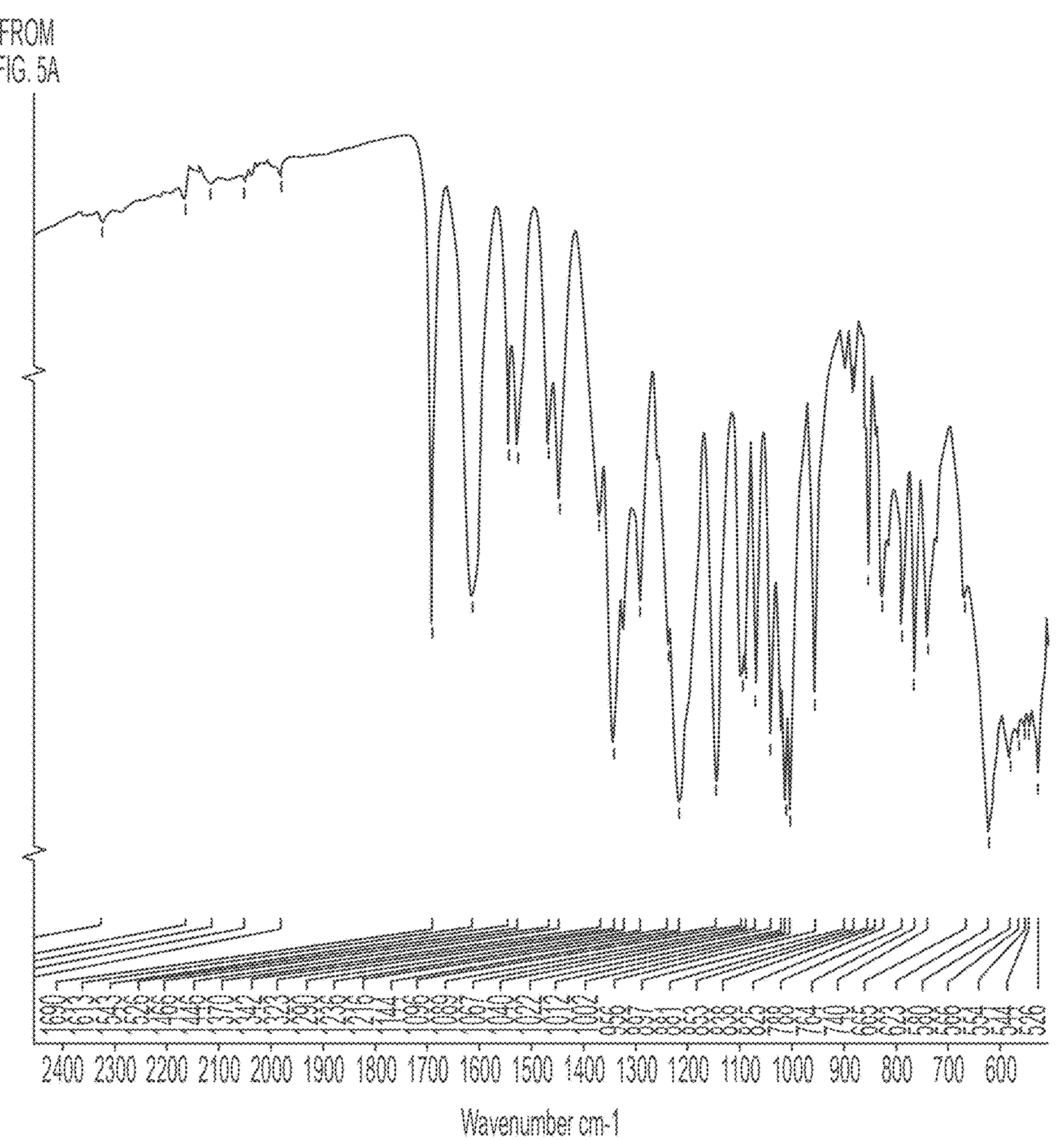

FIGS. 5A and 5B show the infrared spectrum of EGCG Starting Material (Form I).

Figure 6:
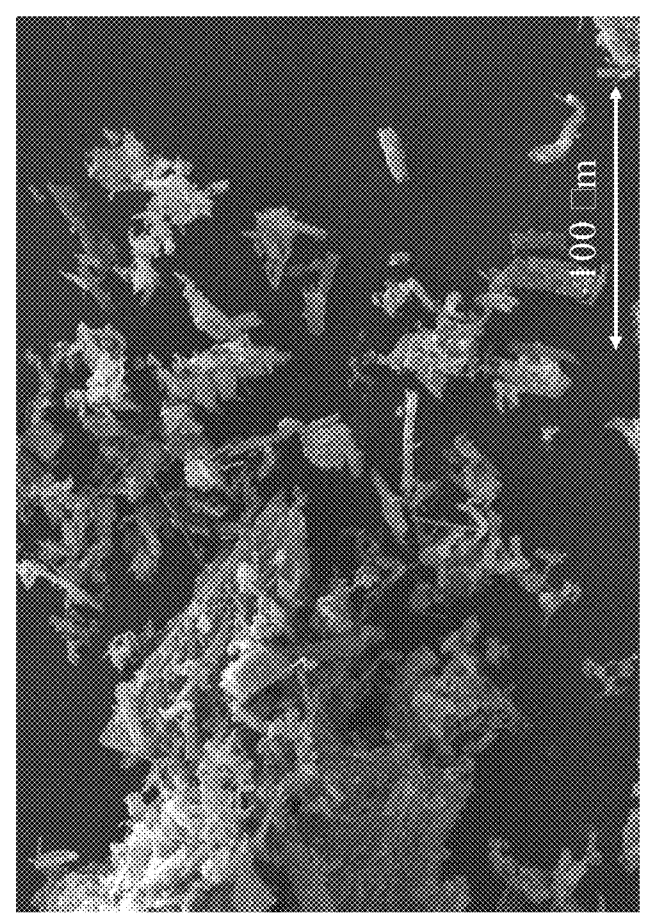
FIG. 6 shows an SEM image of EGCG starting material (Form I).

FIG. 6 shows morphology and particle size. As shown, the EGCG Starting Material (Form I) includes large agglomerated elongated particulates with clear non-uniformity in the particle size distribution. The morphology and agglomeration contribute to its undesirable secondary product characteristics such as its poor flow properties and slow dissolution rate. The morphology, particle size and particle size distribution is not preferable for local delivery to the intestine, where smaller particles and a tabular like morphology are preferred, and its low surface area contributes to a slower dissolution which is inadequate for systemic delivery.

mSAS® Form I

Figure 7:
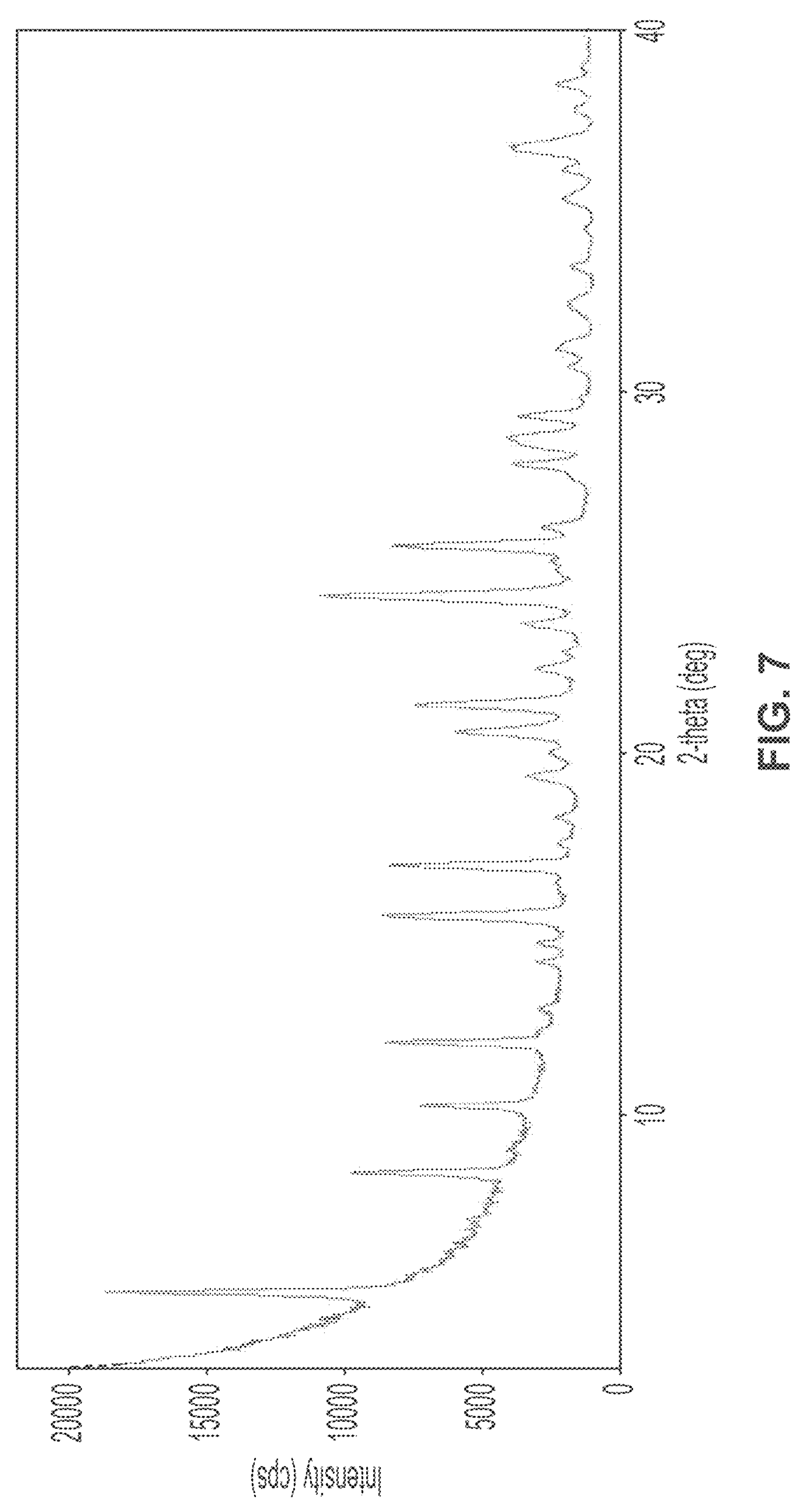
FIG. 7 shows the PXRD pattern of mSAS® Form I.

The PXRD pattern of mSAS® Form I is shown in FIG. 7. Peak positions are set out in Table 3 below.

TABLE 3

| 2-theta (°) | Relative intensity (a.u.) |
|---|---|
| 5.14 | 1555.43 |
| 8.46 | 728.97 |
| 9.08 | 30.67 |
| 10.3 | 566.1 |
| 12.08 | 866.66 |
| 13 | 69.87 |
| 14.3 | 97.8 |
| 14.82 | 110.34 |
| 15.58 | 1177.18 |
| 16.46 | 125.06 |
| 16.98 | 975.7 |
| 17.6 | 48.09 |
| 18.32 | 63.43 |
| 19.46 | 346.06 |
| 20.1 | 175.35 |
| 20.7 | 1013.79 |

TABLE 3-continued

| 2-theta (°) | Relative intensity (a.u.) |
|---|---|
| 21.44 | 1247.24 |
| 22.44 | 203.54 |
| 23.68 | 313.83 |
| 24.46 | 1903.64 |
| 25.16 | 68.35 |
| 25.42 | 75.34 |
| 25.84 | 1166.84 |
| 26.34 | 283.87 |
| 28.12 | 436.49 |
| 28.84 | 874.1 |
| 29.48 | 408 |
| 29.92 | 41.06 |
| 30.82 | 112.28 |
| 31.38 | 309.8 |
| 32.54 | 242.66 |
| 33.6 | 115.69 |
| 34.02 | 16.2 |

Selected characteristic X-ray diffraction peaks for mSAS® form I are 5.1°, 8.5°, and 12.1° 2θ (±0.2° 2θ).

Figure 8:
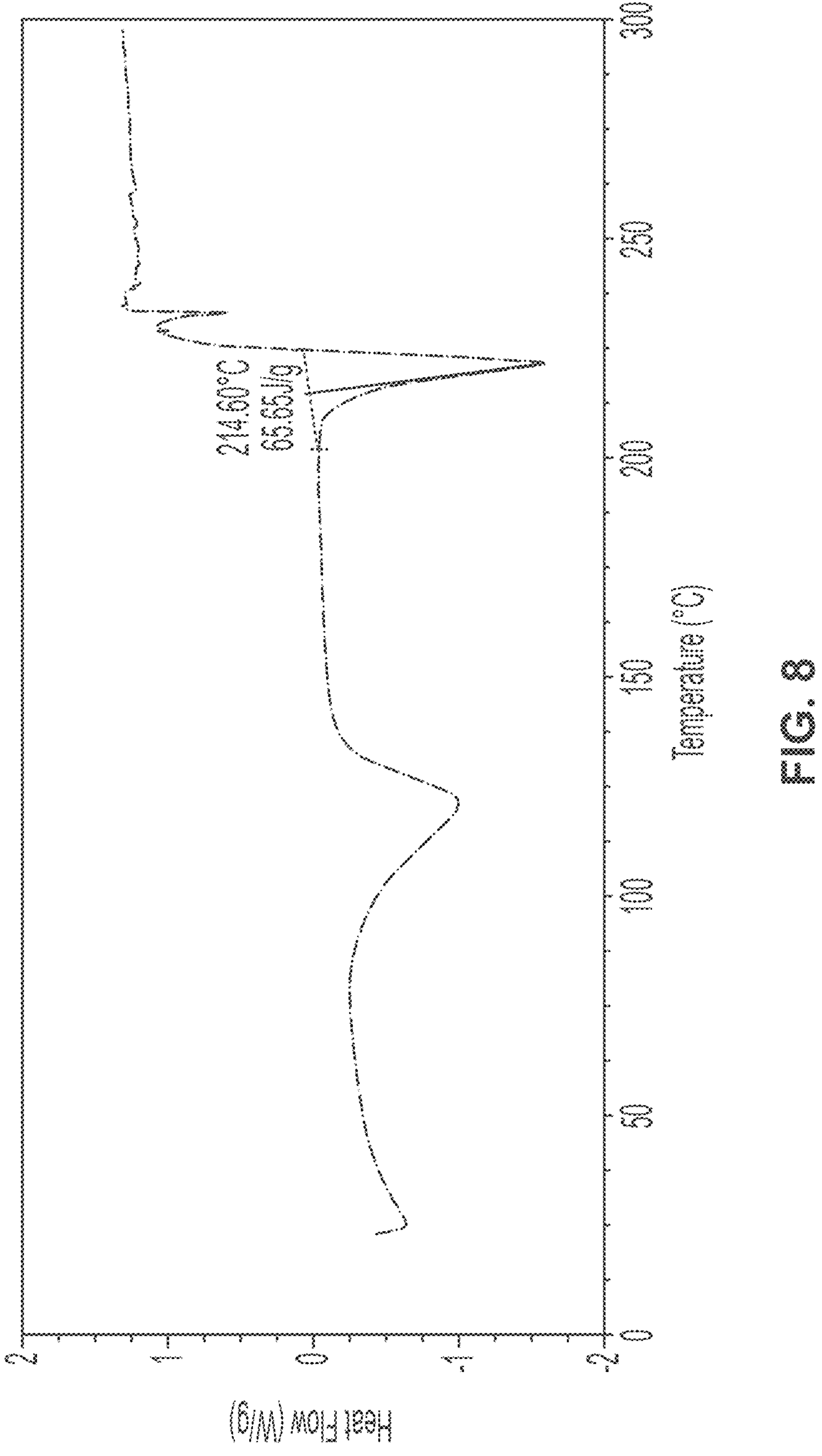
FIG. 8 shows the DSC thermal profile of mSAS® Form I.

FIG. 8 shows the thermal analysis of mSAS® Form I. Similar to EGCG Starting Material (Form I), mSAS® Form I appears to initially go through a dehydration step before melting at a higher temperature. Its melting point and enthalpy of fusion are lower than Form X indicating that mSAS® Form I is metastable and its dehydration occurs at a low temperature.

Figure 9A:
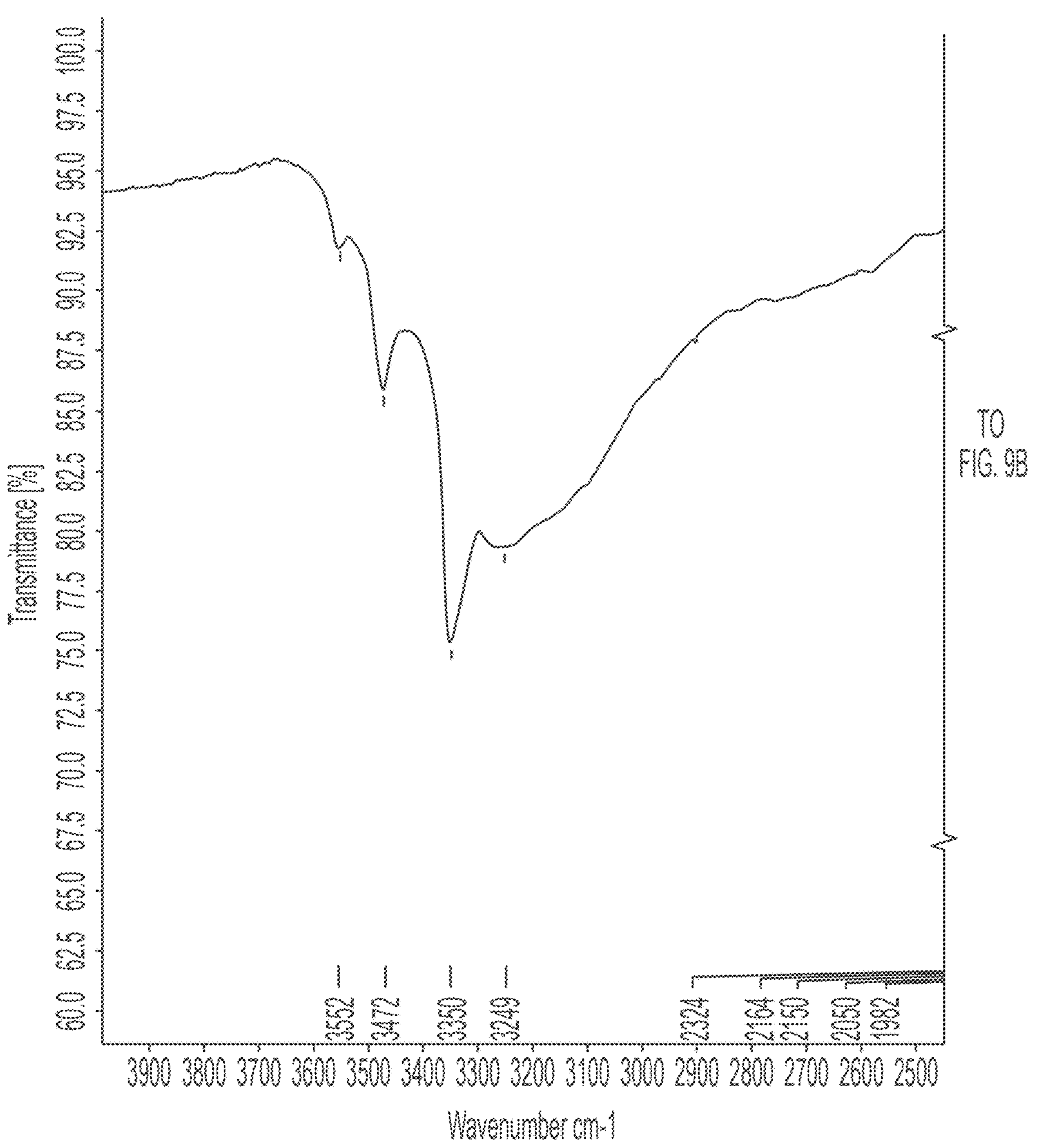
FIGS. 9A and 9B show the FTIR trace of mSAS® Form I.
Figure 9B:
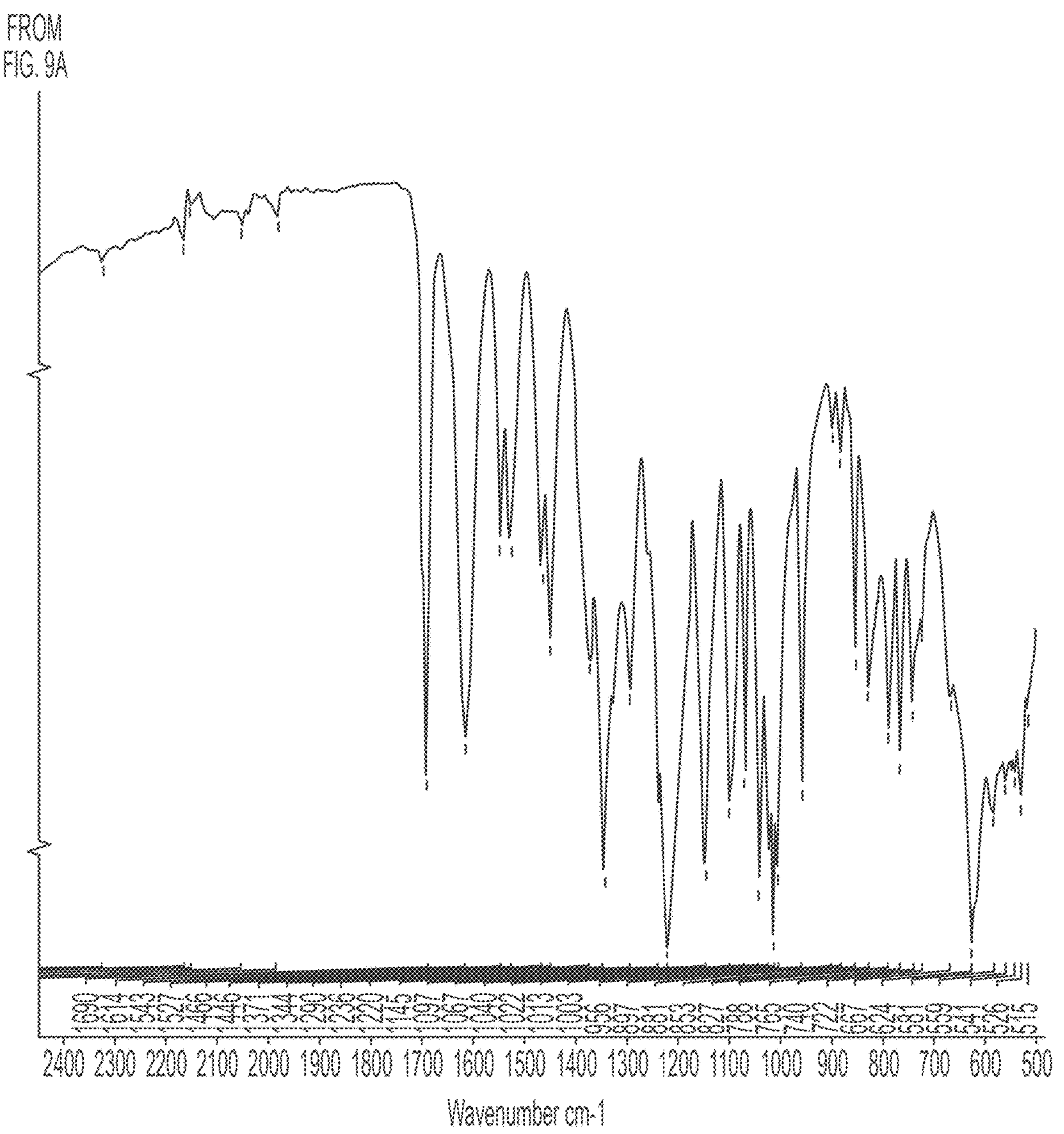

FIGS. 9A and 9B show the infrared spectrum of mSAS® Form I.

Figure 10:
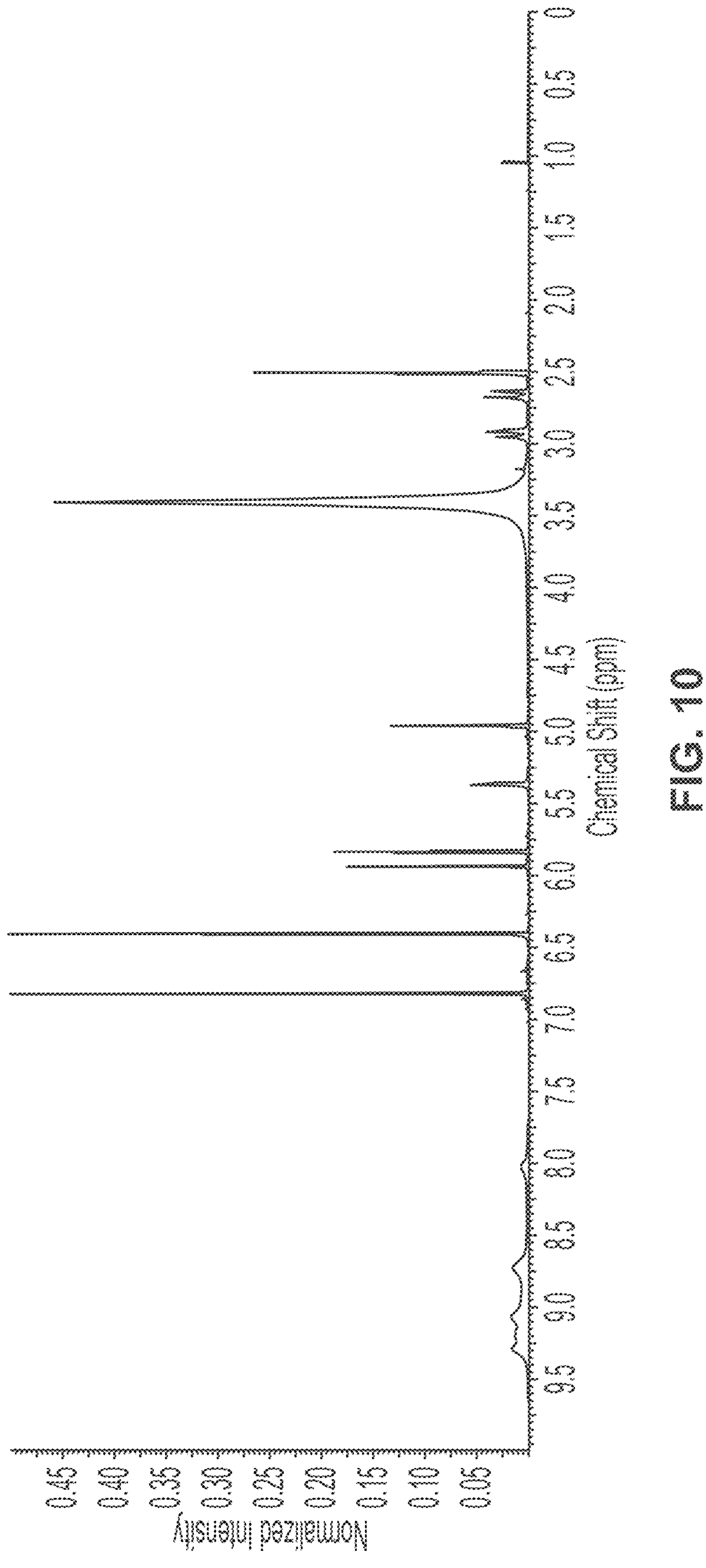
FIG. 10 shows the NMR trace of mSAS® Form I.
Figure 11:
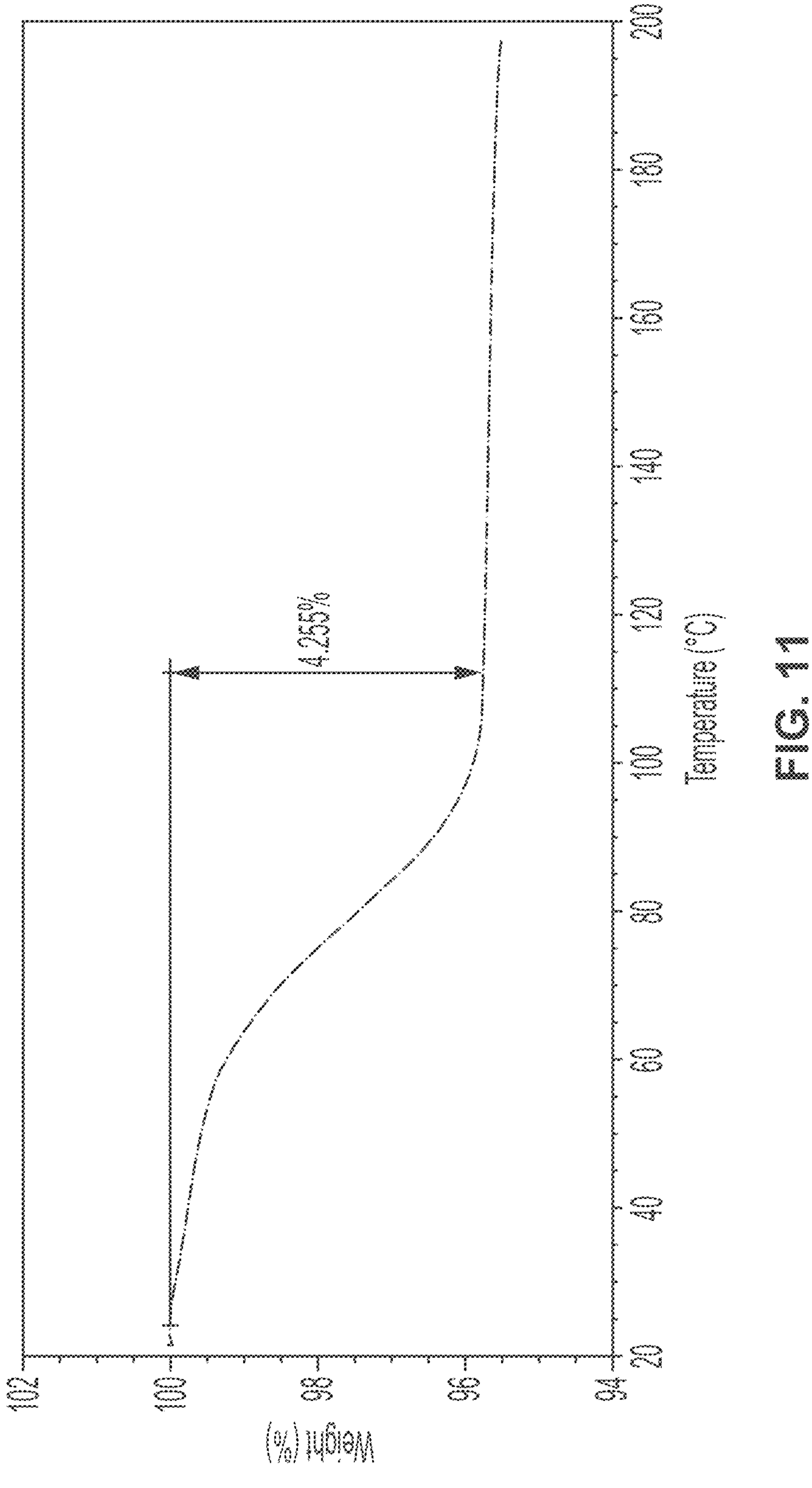
FIG. 11 shows the TGA mass profile of mSAS® Form I.
Figure 12:
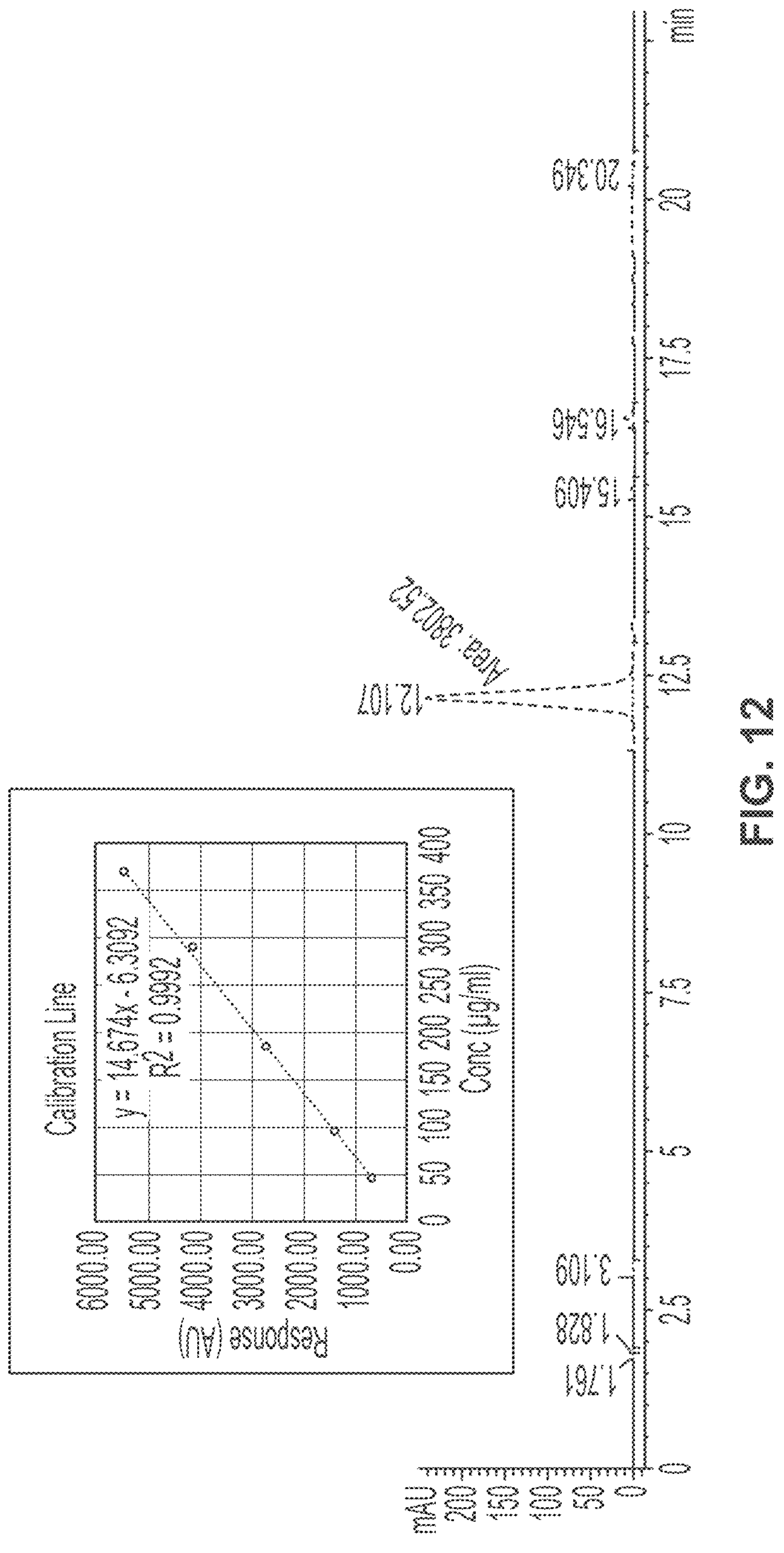
FIG. 12 shows a HPLC trace and calibration curve for mSAS® Form I.

FIGS. 10 and 11 show NMR and TGA profiles of mSAS® Form I, respectively. As shown, the results reveal that there is water and a small amount of isopropanol present. As evidenced by the TGA results in FIG. 11, mSAS® Form I has 4.3% residual solvent. NMR also reveals that there are a number of small impurity peaks which is reflected in the HPLC purity of 97.4% based on dry matter seen in FIG. 12. This was determined from the calculated concentration of 259.71 g/mL from the HPLC compared to the weighed dry amount of 266.72 g/mL. From the NMR alone it can be seen that the impurity peaks are reduced in comparison to the EGCG Starting Material (Form I).

Figure 13:
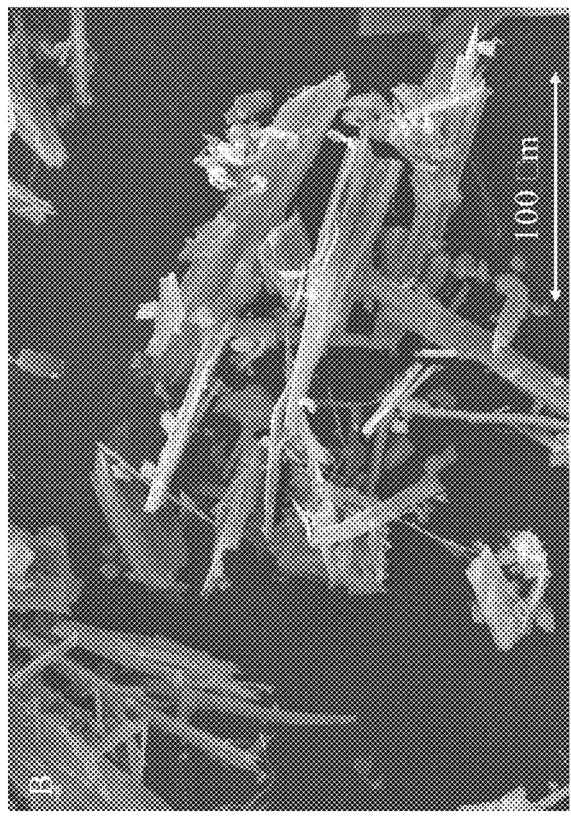
FIG. 13 shows SEM images of mSAS® Form I.
Figure 13:
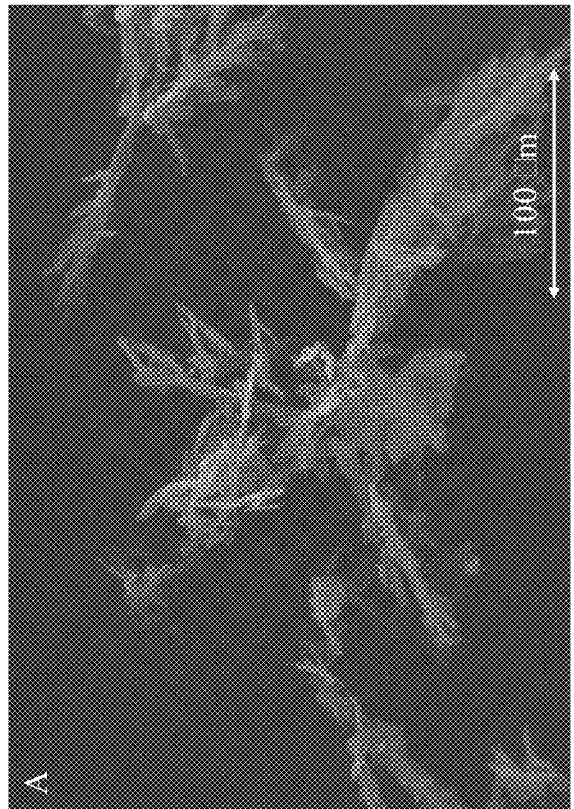

FIG. 13 illustrates morphology and particle size of mSAS® Form I. As shown, mSAS® Form I includes large elongated or needle-like particulates. The non-uniformity in particle size distribution and agglomeration are reduced in comparison to the EGCG Starting Material (Form I) shown in FIG. 6. The morphology and particle size in this case contribute to its undesirable secondary product characteristics such as its poor flow properties and slow dissolution rate. The morphology and particle size is not preferable for local delivery to the intestine, where smaller particles and a tabular like morphology are preferred, and its low surface area contributes to a longer dissolution profile which is inadequate for systemic delivery.

mSAS® Form IV

Figure 14:
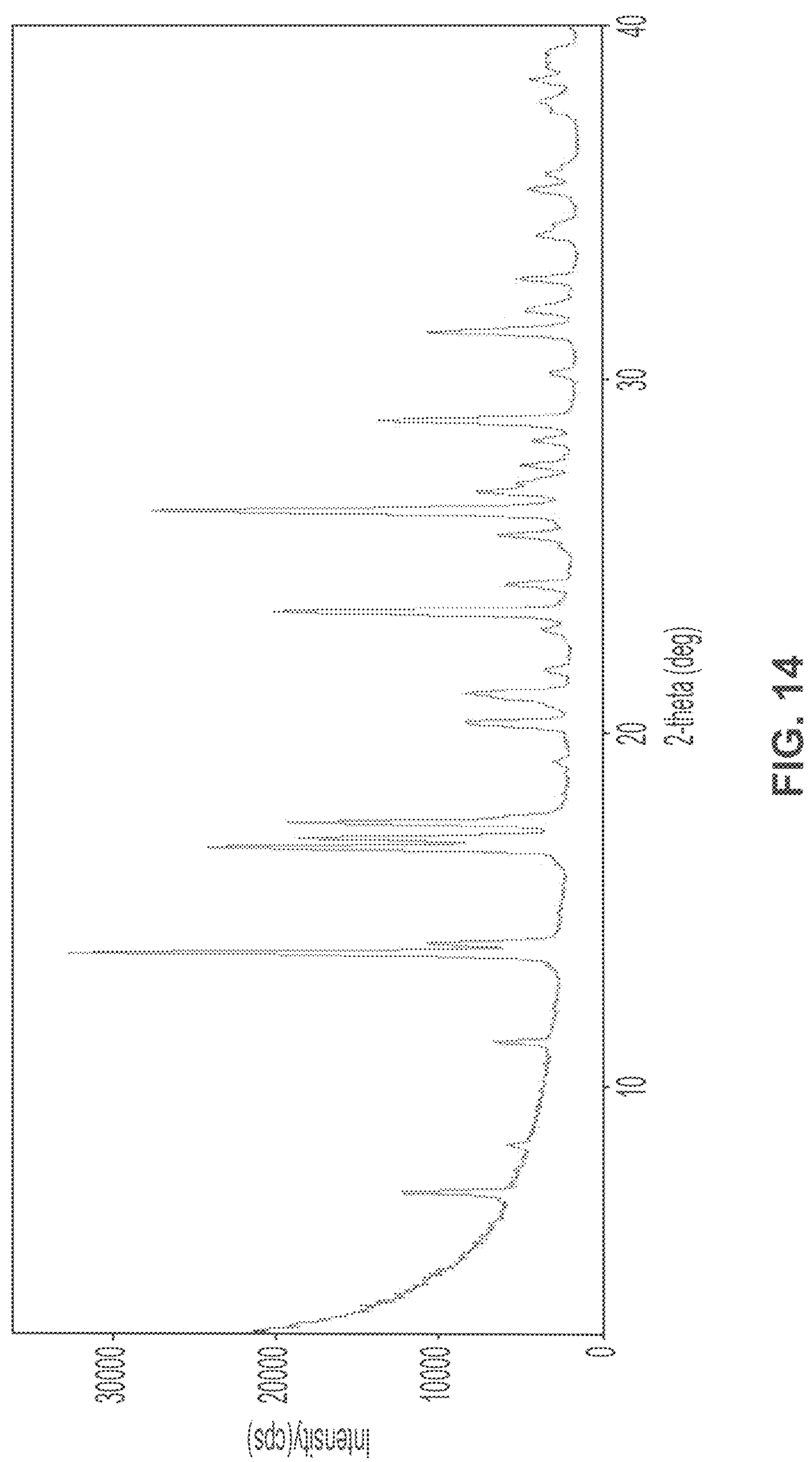
FIG. 14 shows the PXRD pattern of mSAS® Form IV.

The PXRD pattern of Form IV is shown in FIG. 14. Peak positions are set out in Table 4 below.

TABLE 4

| 2-theta (°) | Relative intensity (a.u.) |
|---|---|
| 7.04 | 570.48 |
| 8.36 | 163.5 |
| 11.28 | 367.7 |
| 13.82 | 2011.93 |
| 14.08 | 833.11 |

TABLE 4-continued

| 2-theta (°) | Relative intensity (a.u.) |
|---|---|
| 16.82 | 1768.25 |
| 17.06 | 5098.63 |
| 17.48 | 1456.86 |
| 17.68 | 998.69 |
| 19.24 | 211.33 |
| 19.96 | 36.41 |
| 20.3 | 607.61 |
| 21.04 | 1663.27 |
| 21.78 | 117.5 |
| 22.98 | 489.36 |
| 23.46 | 4925.97 |
| 24.18 | 370.23 |
| 25.62 | 1020.45 |
| 26.3 | 6406.21 |
| 26.9 | 1603.99 |
| 27.58 | 628.66 |
| 28.28 | 235.05 |
| 28.84 | 2580.89 |
| 30.2 | 54.69 |
| 31.36 | 1853.68 |
| 32.06 | 1157 |
| 32.72 | 277.35 |
| 32.86 | 516.38 |
| 34.14 | 430.18 |
| 34.46 | 170.25 |
| 35.34 | 264.79 |
| 35.8 | 188 |
| 36.1 | 226.56 |
| 37.6 | 160.73 |

Selected characteristic X-ray diffraction peaks for mSAS® Form IV are 11.3°, 13.8°, and 14.1° 2θ (±0.2° 2θ).

Figure 15:
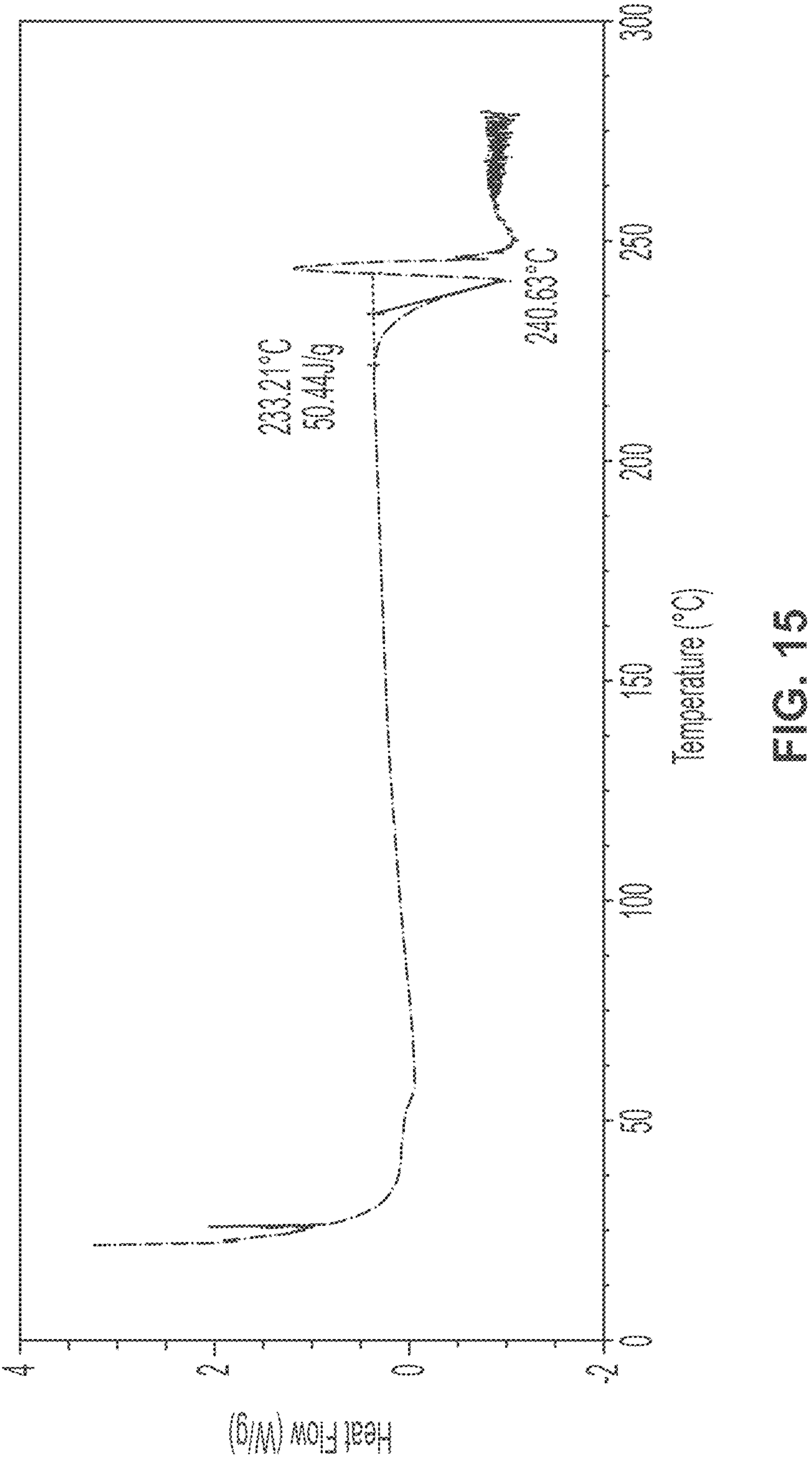
FIG. 15 shows the DSC thermal profile of mSAS® Form IV.

FIG. 15 shows the thermal analysis of mSAS® Form IV. mSAS® Form IV shows a single melting endotherm indicative of an anhydrous polymorph. Its melting point and enthalpy of fusion are lower than Form X indicating that mSAS® Form IV is metastable compared to Form X.

Figure 16A:
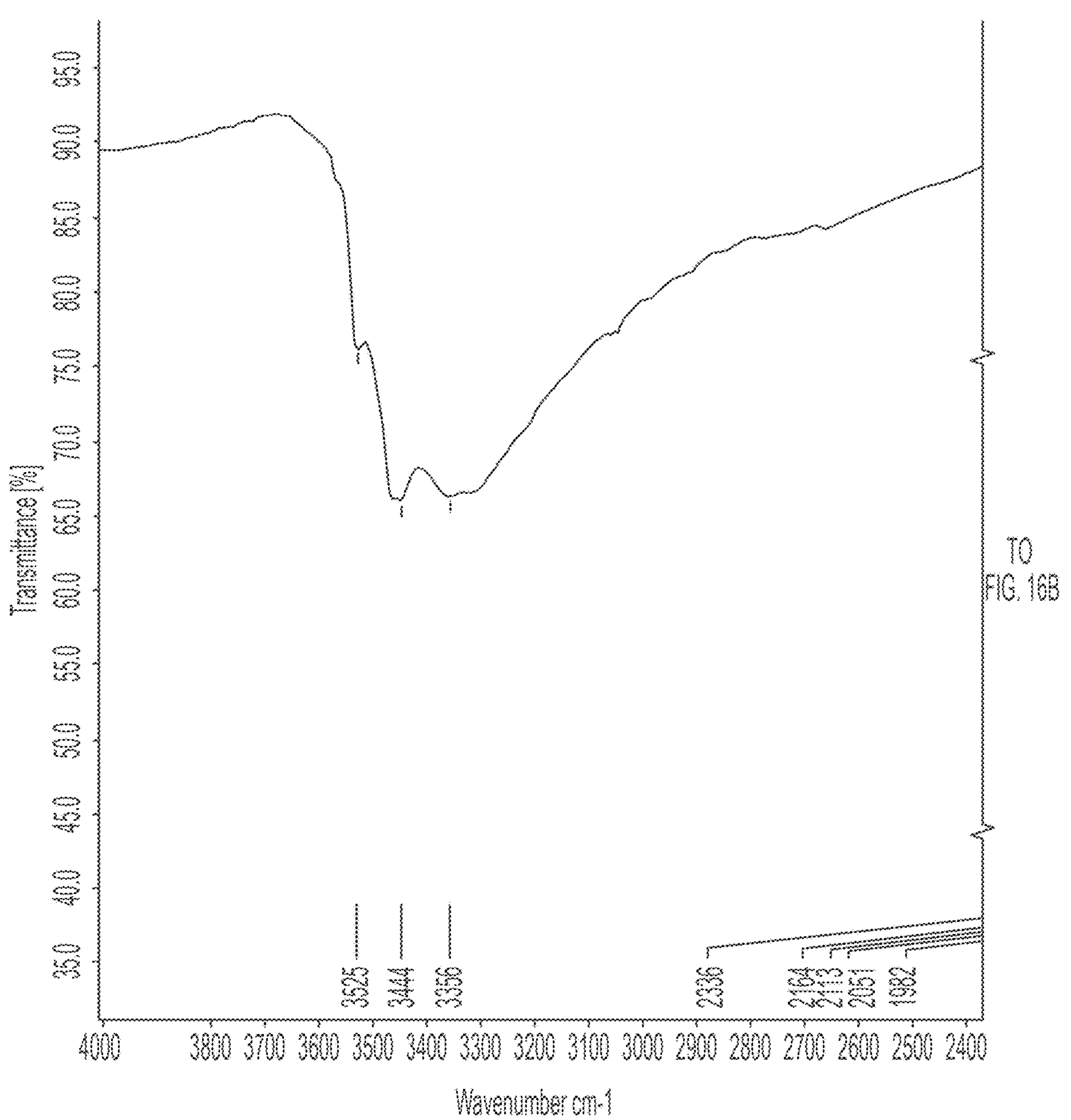
FIGS. 16A and 16B show the FTIR trace of mSAS® Form IV.
Figure 16B:
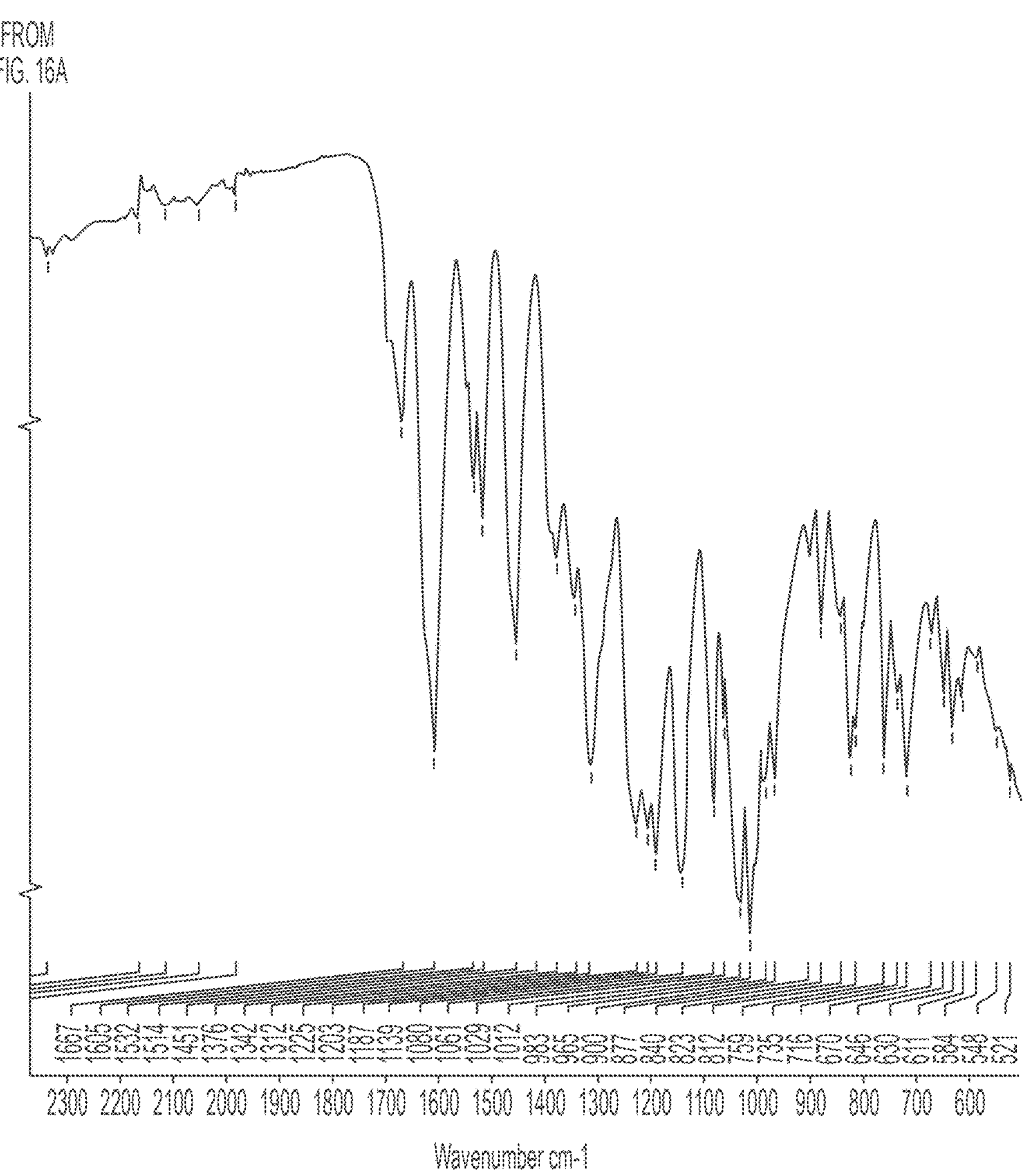

FIGS. 16A and 16B show the infrared spectrum of mSAS® Form IV.

Figure 17:
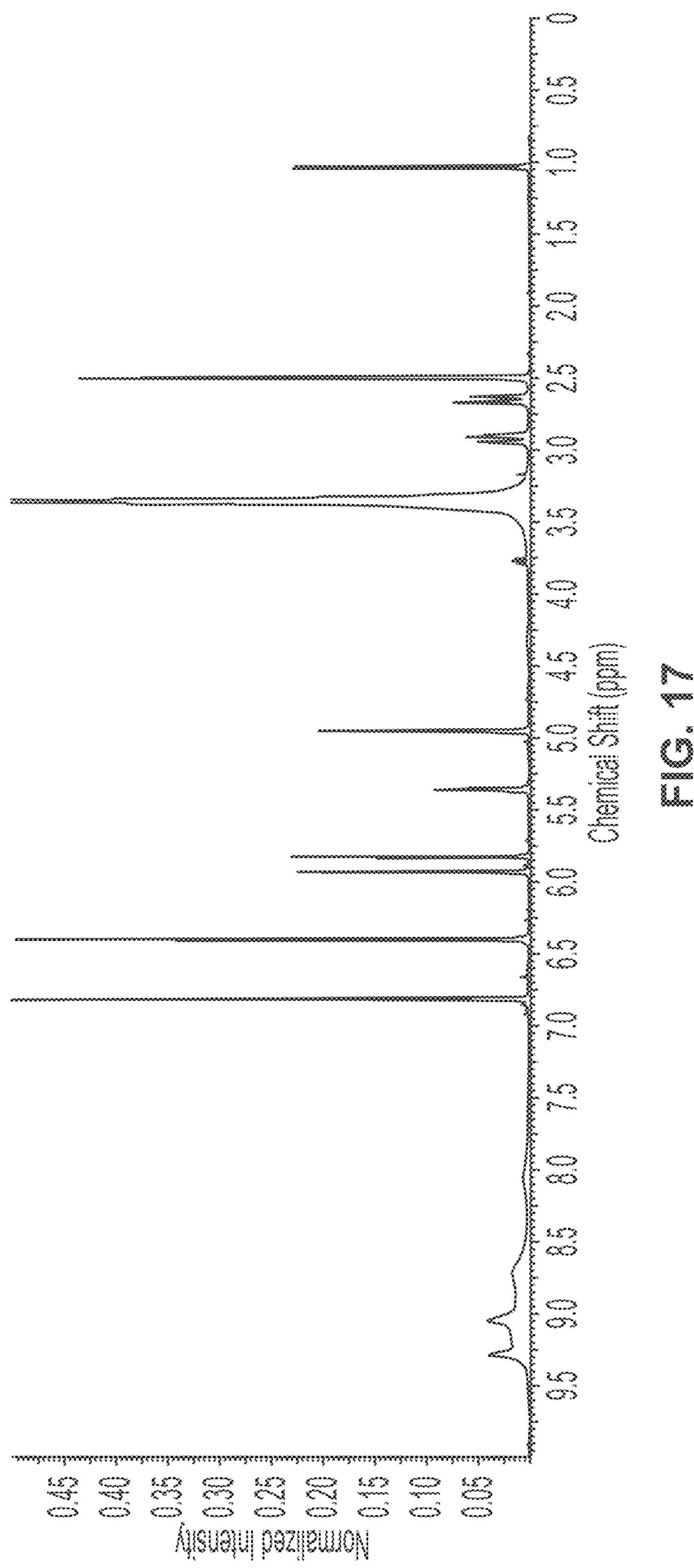
FIG. 17 shows the NMR trace of mSAS® Form IV.
Figure 18:
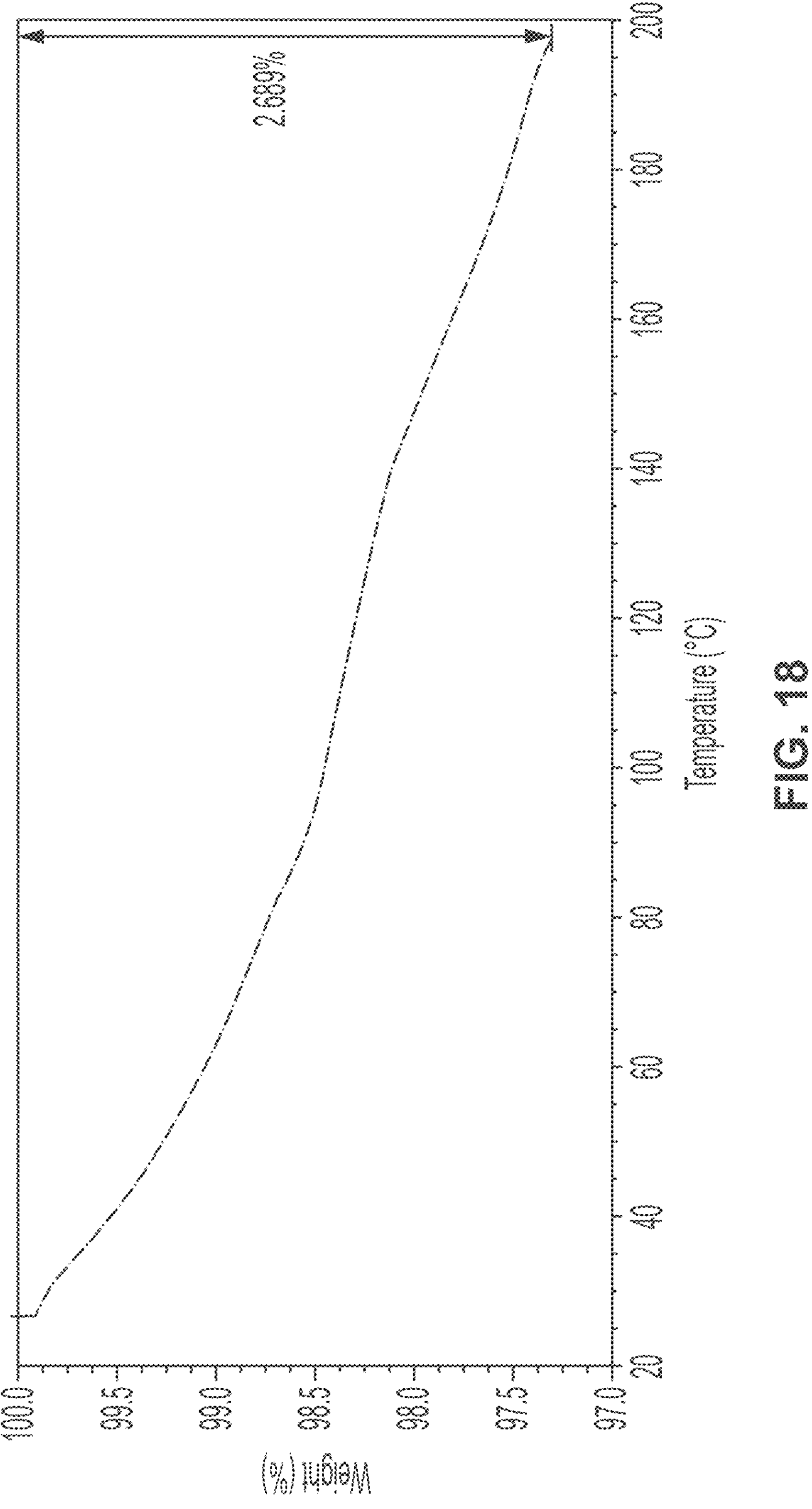
FIG. 18 shows the TGA mass profile of mSAS® Form IV.
Figure 19:
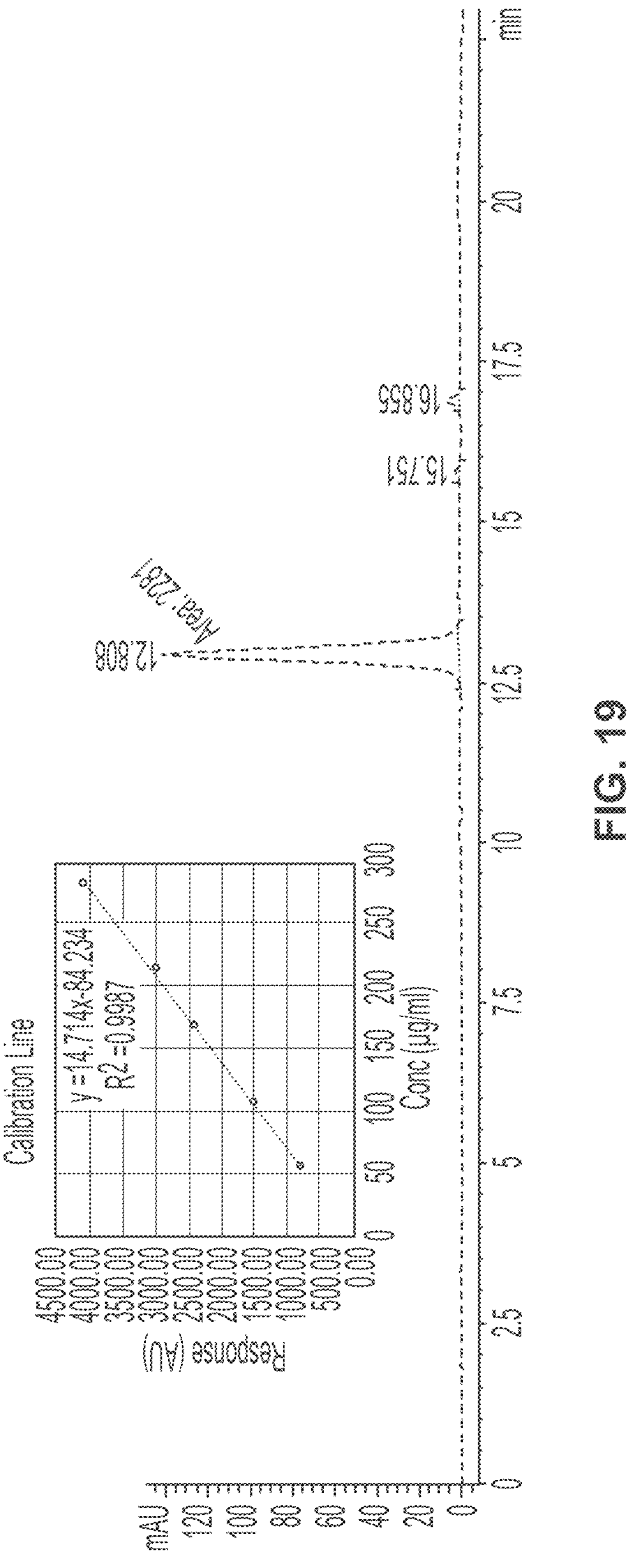
FIG. 19 shows an HPLC trace and calibration curve of mSAS® Form IV.

FIGS. 17 and 18 show NMR and TGA profiles of mSAS® Form IV, respectively. As shown, the results of mSAS® Form IV reveal that there is water and ethanol present. As evidenced by the TGA results in FIG. 18, mSAS® Form IV has 2.7% residual solvent, indicating that this polymorph is prone to solvent inclusion. Its NMR also reveals that there are a number of small impurity peaks which is reflected in the HPLC purity of 96.4% based on dry matter seen in FIG. 19. This was determined from the calculated concentration of 154.36 g/mL from the HPLC compared to the weighed dry amount of 160.17 g/mL. This purity is the lowest out of all of the mSAS® polymorphic forms produced so it could be possible that this crystal lattice is also prone to impurity inclusion. From the NMR alone it can be seen that the impurity peaks are reduced in comparison to the EGCG Starting Material (Form I).

Figure 20:
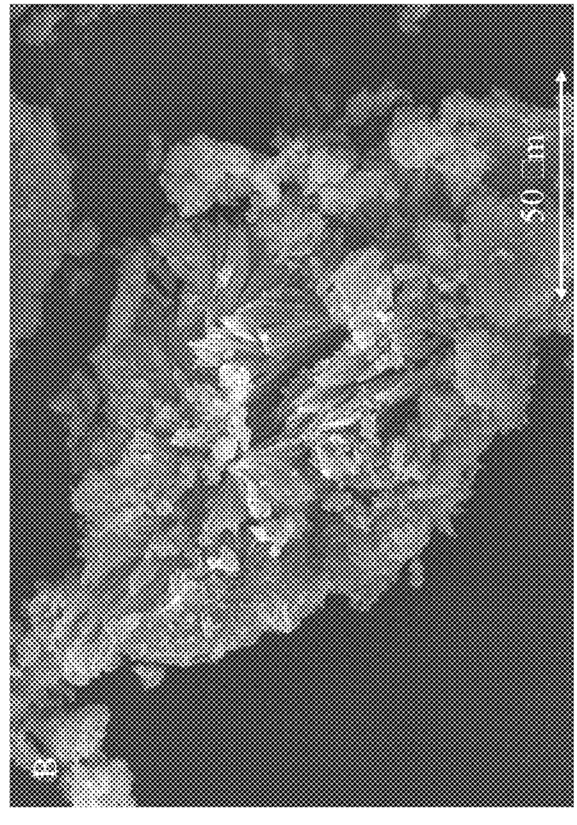
FIG. 20 shows SEM images of mSAS® Form IV.
Figure 20:
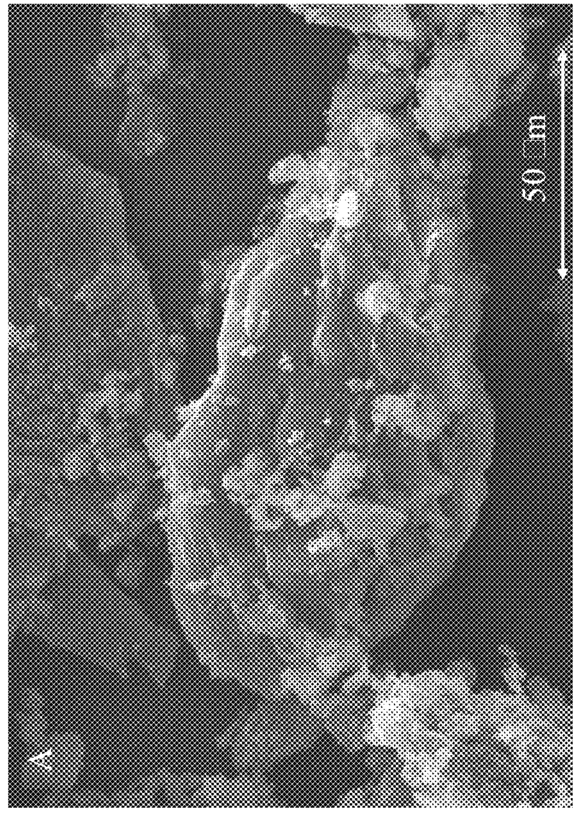

FIG. 20 illustrates morphology and particle size of mSAS® Form IV. As shown, mSAS® Form IV is made up of large agglomerated chunky particulates or agglomerated needle-like feathery particulates. The non-uniformity in particle size distribution and agglomeration are comparable to the EGCG Starting Material (Form I). The morphology and particle size in this case contributes to its undesirable secondary product characteristics such as its poor flow properties. The morphology and particle size is not preferable for local delivery to the intestine, where smaller particles and a tabular like morphology are preferred, and its low surface area contributes to a longer dissolution profile which is inadequate for systemic delivery.

mSAS® Form X

The PXRD pattern of mSAS® Form X is shown in FIG. 21. Peak positions are set out in Table 5 below.

TABLE 5

| 2-theta (°) | Relative intensity (a.u.) |
|---|---|
| 6.44 | 184.99 |
| 9.66 | 1360.55 |
| 10.58 | 276.35 |
| 13 | 66.89 |
| 15.18 | 1328.79 |
| 16.24 | 236.72 |
| 16.94 | 1362.08 |
| 17.34 | 2169.07 |
| 17.84 | 1108.94 |
| 18.4 | 397.28 |
| 19.56 | 913.27 |
| 19.9 | 1735.98 |
| 20.26 | 915.31 |
| 21.62 | 1155.2 |
| 22.18 | 1063.44 |
| 22.72 | 186.74 |
| 23.02 | 109.7 |
| 23.76 | 1796.79 |
| 24.26 | 1067.64 |
| 24.54 | 2386.9 |
| 25.04 | 177.08 |
| 26.12 | 1180.07 |
| 26.46 | 2571.67 |
| 27.54 | 404.32 |
| 28.32 | 10.4 |
| 28.66 | 220.23 |
| 29.28 | 540.39 |
| 29.58 | 286.81 |
| 30.08 | 548.8 |
| 30.32 | 23.4 |
| 31.54 | 265.58 |
| 31.9 | 1361.12 |
| 32.86 | 253.04 |

Selected characteristic X-ray diffraction peaks for mSAS® Form X are 6.4°, 9.7°, and 10.6° 2θ (±0.2° 2θ).

FIG. 22 shows the thermal analysis of mSAS® Form X. mSAS® Form X shows a single melting endotherm indicative of an anhydrous polymorph. Its melting point and enthalpy of fusion are higher than either Form I or Form IV indicating that mSAS® Form X is the most stable polymorphic form.

FIGS. 23A and 23B show the infrared spectrum of mSAS® Form X.

FIGS. 24 and 25 show NMR and TGA profiles for Form X, respectively. As shown, the results reveal that there is water and a small amount of isopropanol present. The residual solvent content is around 0.9%. The Form X NMR also reveals that there are a number of small impurity peaks which is reflected in the HPLC purity of 98.7% based on dry matter seen in FIG. 26. This was determined from the calculated concentration of 202.1 g/mL from the HPLC compared to the weighed dry amount of 204.7 g/mL. From the NMR alone it can be seen that the impurity peaks are reduced in comparison to the EGCG Starting Material (Form I). Its purity is the highest out of all the mSAS® samples tested and is considered acceptable from a regulatory standpoint.

The Form X morphology and particle size seen in FIG. 27 comprises of small tabular particles. Its particle size distribution and agglomeration appear to be reduced in comparison to EGCG Starting Material (Form I) and other mSAS® polymorphic Forms I and IV. The morphology and particle size of Form X contribute to its more desirable product characteristics such as its enhanced flow properties and fast dissolution profile. The morphology and particle size of Form X is beneficial for local delivery to the intestine, where smaller particles and a tabular like morphology are preferred, and the low surface area of Form X contributes to a shorter dissolution profile which may be advantageous for systemic delivery.

Comparative Analysis

Rate of dissolution tests were performed using 70 mg of crystalline sample that was weighed into a stoppered 20 mL glass scintillation vial with a stirrer bar. 3.5 mL of water was pipetted into the vial and the contents stirred at 700 RPM at room temperature until a clear solution could be observed.

| Material | Time to Dissolve (min) |
|---|---|
| EGCG Starting Material (Form I) | Insoluble (Did not dissolve fully after 30 minutes) |
| mSAS ® Form I | Insoluble (Did not dissolve fully after 30 minutes) |
| mSAS ® Form IV | 4.5 |
| mSAS ® Form X | 3 |

Figure 28:
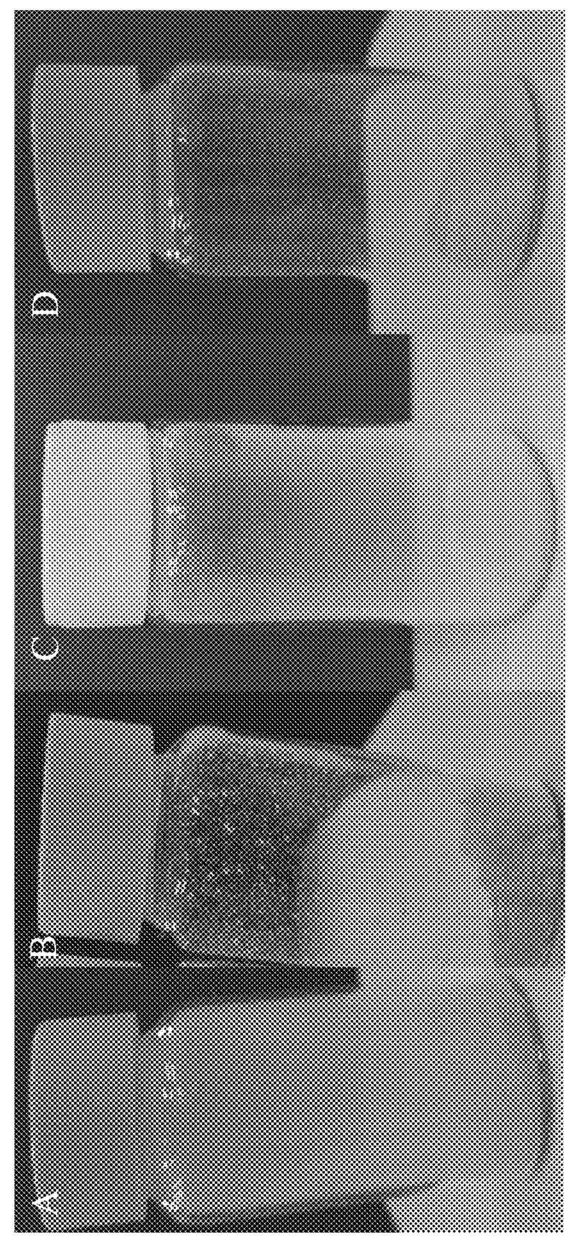
FIG. 28 shows adherence of particles to vials for EGCG Starting Material (Form I), mSAS® Form I, mSAS® Form IV, and mSAS® Form X after flow experiments.

Powder handling and flow testing was performed on 70 mg of crystalline sample that was weighed into a stoppered 20 mL glass scintillation vial. Each vial was rotated for 20 seconds on its side making sure the crystalline powder covered the length of the vial. Images were taken of the vials afterwards as can be seen in FIG. 28.

EGCG Starting Material (Form I) (A) had the worst flow properties followed by mSAS® Form I (B), then mSAS® Form IV (C), and finally mSAS® Form X (D), which had the best flow properties.

Embodiment 1: Crystalline Form X epigallocatechin-3-gallate.

Embodiment 2: A method of preparing crystalline Form X epigallocatechin-3-gallate, the method comprising contacting a fluid anti-solvent with a solution comprising the compound of Formula I in a solvent, to precipitate said crystalline form of the compound of Formula I.

Embodiment 3: The method of embodiment 2, wherein the anti-solvent is a supercritical fluid.

Embodiment 4: The method of embodiment 2, wherein the solution comprises a natural starting material, optionally a tea extract.

Embodiment 5: The method of embodiment 4, wherein the starting material has a chemical purity of the epigallocatechin-3-gallate of at least 85%.

Embodiment 6: The method of embodiment 5, wherein the starting material has a chemical purity of the epigallocatechin-3-gallate of at most 95.4%.

Embodiment 7: The method of embodiment 2, wherein the solution is formed from a starting material comprising a crystalline form of the epigallocatechin-3-gallate having an x-ray powder diffraction pattern with peaks at 2θ values of about 5.2°, 8.5° and 12.1°.

Embodiment 8: The method of embodiment 2, further comprising:

- providing a stream of the solution of the epigallocatechin-3-gallate to a precipitation chamber;
- providing a stream of the fluid anti-solvent to the precipitation chamber; and
- contacting the stream of the solution with the stream of the fluid anti-solvent within the precipitation chamber to precipitate said crystalline Form X of epigallocatechin-3-gallate within the precipitation chamber.

Embodiment 9: The method of embodiment 2, wherein the anti-solvent comprises carbon dioxide.

Embodiment 10: The method of embodiment 2, wherein the anti-solvent comprises carbon dioxide having a pressure of from 85 to 205 bar absolute and a temperature of from 40° C. to 95° C.

Embodiment 11: The method of embodiment 2, wherein the anti-solvent and the solution are cofed into a precipitation chamber via a nozzle having co-axial passages which terminate adjacent to one another.

Embodiment 12: The method of embodiment 2, wherein one or more streams of the anti-solvent are arranged to impinge on a stream of the solution.

Embodiment 13. A pharmaceutical composition comprising crystalline Form X epigallocatechin-3-gallate and a pharmaceutically acceptable carrier and/or excipient.

Embodiment 14: A method for treating, preventing, slowing the onset of, and/or slowing the progression of a condition or disease for which epigallocatechin-3-gallate is known to be effective in a human patient in need thereof, the method comprising administering an effective amount of Form X epigallocatetchin-3-gallate to said human patient.

Embodiment 15. A method for reducing inflammation in a human patient in need thereof, comprising administering to said human an effective amount of Form X epigallocatechin-3-gallate.

The invention claimed is:

1. Crystalline Form X epigallocatechin-3-gallate characterized by an X-ray diffraction (XRPD) pattern having peaks at 6.4° , 9.7° , and 10.6° 2θ (±0.2° 2θ).

* * * * *